(12) United States Patent
Blumenkranz

(10) Patent No.: US 8,561,473 B2
(45) Date of Patent: *Oct. 22, 2013

(54) FORCE SENSOR TEMPERATURE COMPENSATION

(75) Inventor: Stephen J Blumenkranz, Redwood City, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1227 days.

This patent is subject to a terminal disclaimer.

(21) Appl. No.: 12/414,534

(22) Filed: Mar. 30, 2009

(65) Prior Publication Data

US 2009/0192522 A1 Jul. 30, 2009

Related U.S. Application Data

(63) Continuation-in-part of application No. 11/958,772, filed on Dec. 18, 2007.

(51) Int. Cl.
*G01B 11/16* (2006.01)
*A61B 19/00* (2006.01)
*G01L 1/24* (2006.01)

(52) U.S. Cl.
USPC ............ 73/800; 73/760; 73/856; 73/862.624; 606/1; 606/130; 385/13; 385/54

(58) Field of Classification Search
None
See application file for complete search history.

(56) References Cited

U.S. PATENT DOCUMENTS

| | | | |
|---|---|---|---|
| 3,764,354 A | 10/1973 | Ritze et al. | |
| 4,448,083 A * | 5/1984 | Hayashi | 73/862.042 |
| 5,488,475 A | 1/1996 | Friebele et al. | |
| 6,417,963 B1 * | 7/2002 | Ohishi et al. | 359/341.1 |
| 6,668,105 B2 * | 12/2003 | Chen et al. | 385/13 |
| 6,836,356 B2 | 12/2004 | Jiang et al. | |
| 6,987,895 B2 | 1/2006 | Johannessen | |
| 7,046,887 B2 * | 5/2006 | Kawanishi et al. | 385/125 |
| 7,302,139 B1 * | 11/2007 | Ames | 385/37 |

(Continued)

FOREIGN PATENT DOCUMENTS

WO 2007120329 A2 10/2007

OTHER PUBLICATIONS

"Strain and Temperature Sensitive of a Single-mode Polymer Optical Fiber", Manuel Silva-Lopez et al., Optics Letters, Dec. 1 2005, vol. 30, No. 23 p. 3129-3131.*

(Continued)

*Primary Examiner* — Sam Yao
*Assistant Examiner* — Boniface N Nganga

(57) ABSTRACT

In one embodiment, a force sensor apparatus is provided including a tube portion having a plurality of radial ribs and at least one fiber optic strain gauge positioned over each rib of the plurality of radial ribs. The strain gauges are comprised of a negative thermo-optic coefficient optical fiber material in one embodiment. A proximal end of the tube portion is operably couplable to a shaft of a surgical instrument that is operably couplable to a manipulator arm of a robotic surgical system, and a distal end of the tube portion is proximally couplable to a wrist joint coupled to an end effector. In another embodiment, adjacent fiber optic strain gauges with differing thermal responses are used to solve simultaneous equations in strain and temperature to derive strain while rejecting thermal effects. In yet another embodiment, a thermal shunt shell is over an outer surface of the tube portion. An advantageous surgical instrument having improved temperature compensation is also provided.

15 Claims, 19 Drawing Sheets

(56) References Cited

U.S. PATENT DOCUMENTS

| | | | |
|---|---|---|---|
| 7,382,957 B2 * | 6/2008 | Chen et al. | 385/123 |
| 7,743,672 B2 * | 6/2010 | Kurtz et al. | 73/862.046 |
| 2007/0183464 A1 | 8/2007 | Poulsen et al. | |

OTHER PUBLICATIONS

Abe, Ilda et al., "Three-Parameter Simultaneous Measurement Using Superimposed Bragg Gratings in High-birefringence Optical Fibers", 16th International Conference on Optical Fiber Sensors, Oct. 13-17, 2003, Nara, Japan, 4 Pages.

Abe, Ilda et al., "Characterization of FBGs written in HiBi IEC fibre for multiparameter sensors," 15th Annual Meeting of the IEEE Lasers and Electro-Optics Society, Nov. 10-14, 2002, vol. 1, pp. 173-174.

Abe, Ilda et al., "Production and characterisation of Bragg gratings written in high-birefringence fibre optics," IEE Proceedings—Circuits, Devices and Systems, Dec. 4, 2003, vol. 150, Issue 6, pp. 495-500.

Albert, J. et al., "Strong Bragg gratings in phosphate glass single mode fiber," Applied Physics Letters, vol. 89, pp. 101127-1 through 101127-3, posted online Sep. 8, 2006.

Androz, Guillaume et al., Abstract of "Monolithic fluoride-fiber laser at 1480 nm using fiber Bragg," Optics Letters, vol. 32, Issue 10, p. 1302, Apr. 17, 2007.

Arain, M.A. et al, "A Note on Substrate Thermal Lensing Compensation using Negative Thermo-optic Coefficient Material," Laser Interferometer Gravitational Wave Observatory (LIGO), An internal working note of the LIGO project, LIGO-T060077-00-Z, pp. 1-13, Mar. 14, 2006.

Bar-Cohen, Avram et al., "Thermo-Optic Effects in Polymer Bragg Gratings," Chapter 2 in Micro- and Opto-Electronic Materials and Structures: Physics, Mechanics, Design, Reliability, Packaging, Eds. E. Suhir et al., Pub. Springer US, 2007, pp. 65-110.

Bernier, M. et al., "Writing of fiber Bragg gratings in fluoride glass fibers," Optics and Photonics Congress and Exhibit/Bragg Gratings, Photosensitivity and Poling (OSA/BGG 2007), in Bragg Gratings, Photosensitivity, and Poling in Glass Waveguides, OSA Technical Digest (CD) Optical Society of America, 2007, paper BTuC5, 3 pages.

Besley, James A. et al., "Fiber Cladding Mode Sensitivity Characterization for Long-Period Gratings," Journal of Lightwave Technology, vol. 21, No. 3, Mar. 2003, pp. 848-853.

Betz, Daniel C. et al., "Advanced Layout of a Fiber Bragg Grating Strain Gauge Rosette," Journal of Lightwave Technology, vol. 24, No. 3, Feb. 2006, pp. 1019-1026.

Brady, G.P. et al., "Simultaneous measurement of strain and temperature using the first- and second-order diffraction wavelengths of Bragg gratings," IEE Proceedings Optoelectronics, vol. 144, No. 3, Jun. 1997, pp. 156-161.

Cavaleiro, P.M. et al., "Simultaneous Measurement of Strain and Temperature Using Bragg Gratings Written in Germanosilicate and Boron-Codoped Germanosilicate Fibers," IEEE Photonics Technology Letters, vol. 11, No. 12, Dec. 1999, pp. 1635-1637.

Chen, Guanghui et al., "Simultaneous Strain and Temperature Measurements With Fiber Bragg Grating Written in Novel Hi-Bi Optical Fiber," IEEE Photonics Technology Letters, vol. 16, No. 1, pp. 221-223, Jan. 2004.

Chiang, Y.J. et al., "Temperature-Insensitive Multipoint Strain-Sensing System Based on Fiber Bragg Gratings and Optical Power Detection Scheme," IEEE Sensors Journal, vol. 6, No. 2, pp. 465-470, Apr. 2006.

Chmielewska, Ewa et al., "Sensitivity of Bragg Grating Imprinted in a Three-Mode Elliptical Core Fiber to Temperature and to Strain," Proceedings of 2003 5th International Conference on Transparent Optical Networks, Jun. 29-Jul. 3, 2003, vol. 1, pp. 283-286.

Chojetzki, C. et al., "Temperature dependence of type I-IA dual-fibre Bragg gratings," Electronics Letters, Dec. 9, 2004, vol. 40, No. 25, 2 Pages.

Dai, Shixun et al., "Study of a new ytterbium doped phosphate laser glass," Chinese Science Bulletin, vol. 47, No. 3, pp. 255-259, Feb. 2002.

Davis, M.A. and A.D. Kersey, "Simultaneous measurement of temperature and strain using fibre Bragg gratings and Brillouin scattering," IEE Proceedings Optoelectron., vol. 144, No. 3, pp. 151-155, Jun. 1997.

Dobb, H. et al., "Temperature-insensitive long period grating sensors in photonic crystal fibre," Electronics Letters, May 27, 2004, vol. 40, No. 11, 2 Pages.

Du, Wei-Chong et al., "Fiber Bragg Grating Cavity Sensor for Simultaneous Measurement of Strain and Temperature," IEEE Photonics Technology Letters, vol. 11, No. 1, pp. 105-107, Jan. 1999.

Du, Wei-Chong et al., "Temperature Independent Strain Measurement with a Fiber Grating Tapered Cavity Sensor," IEEE Photonics Technology Letters, vol. 11, No. 5, pp. 596-598, May 1999.

Echevarria, J. et al., "Efficient Temperature and Strain Discrimination with a Single Type I Fiber Bragg Grating Transducer," 13th Annual Meeting IEEE Lasers and Electro-Optics Society 2000 Annual Meeting (LEOS-2000), Nov. 13-16, 2000, vol. 2, pp. 458-459.

Echevarria, J. et al., "Uniform Fiber Bragg Grating First- and Second-Order Diffraction Wavelength Experimental Characterization for Strain-Temperature Discrimination," IEEE Photonics Technology Letters, vol. 13, No. 7, pp. 696-698, Jul. 2001.

Eldada, Louay, "Advances in Telecom and datacom optical components," Optical Engineering, vol. 40, Issue 7, pp. 1165-1178, Jul. 2001.

Eldada, Louay, "Optical Networking Components," Sep. 2, 2005, 22 pages, Internet: http://photonics.dupont.com/downloads/OpticalNetworkingComponents.pdf.

Forsyth, David I. et al., "Dual temperature and strain measurement with the combined fluorescence lifetime and Bragg wavelength shift approach in doped optical fiber," Applied Optics, Nov. 1, 2002, vol. 41, No. 31, pp. 6585-6592.

Frank, Andreas et al., "Novel Methods for Simultaneous Strain and Temperature Measurements with Optical Fiber Bragg Gratings," SPIE Conference on Fiber Optic Sensor Technology and Applications, Boston, Massachusetts, Sep. 1999, SPIE vol. 3860, pp. 89-97.

Frazao, O. and J.L. Santos, "Simultaneous measurement of strain and temperature using a Bragg grating structure written in germanosilicate fibres," Journal of Optics A: Pure and Applied Optics, vol. 6, pp. 553-556, 2004.

Frazao, O. et al., "Discrimination of strain and temperature using Bragg gratings in microstructured and standard optical fibres," Measurement Science and Technology, vol. 16, pp. 2109-2113, 2005.

Frazao, O. et al., "Fiber ring laser sensor for strain-temperature discrimination based on four-wave mixing effect," Optical Engineering, vol. 46, Issue 1, pp. 01052-1 through 01052-3, Jan. 2007.

Frazao, O. et al., "Sampled fibre Bragg grating sensors for simultaneous strain and temperature measurement," Electronics Letters, Jul. 4, 2002, vol. 38, No. 14, 2 Pages.

Frazao, O. et al., "Short in-fibre Bragg grating structure for simultaneous measurement of strain and temperature," 17th International Conference on Optical Fibre Sensors, Proceedings of SPIE, vol. 5855, pp. 876-879, 2005.

Frazao, O. et al., "Simultaneous Measurement of Strain and Temperature Based on Polarization Loss Properties of Arc-Induced Long Period Gratings," 2nd European Workshop on Optical Fibre Sensors, Eds. Lopez-Higuera et al., 2004, SPIE vol. 5502, pp. 168-171.

Frazao, O. et al., "Simultaneous measurement of strain and temperature using fibre Bragg gratings in a twisted configuration," Journal of Optics A: Pure and Applied Optics, vol. 7, pp. 427-430, 2005.

Frazao, O. et al., "Simultaneous measurement of strain and temperature using type I and type IIA fibre Bragg gratings," Journal of Optics A: Pure and Applied Optics, vol. 5, pp. 183-185, 2003.

Frazao, O. et al., "Simultaneous measurement of temperature and strain using a step spectrum profile fibre Bragg grating arrangement," 2nd European Workshop on Optical Fibre Sensors, Eds. Lopez-Higuera et al., 2004, SPIE vol. 5502, pp. 132-135.

Frazao, O. et al., "Strain-temperature discrimination using a step spectrum profile fibre Bragg grating arrangement," Sensors and Actuators A: Physical, vol. 120, Issue 2, May 17, 2005, pp. 490-493.

(56) References Cited

OTHER PUBLICATIONS

Goodman, William A, "Phosphate Athermal Glass for Windows and Fibers," Sep. 19, 2006, 14 pages; Internet: http://optics.nasa.gov/tech_days/tech_days_2006/docs/36%20Schafer%20Phosphate%20Athermal%20Glass%20for%20Windows%20and%20Fibers.pdf.
Grattan, Kenneth T.V. et al., "Combined fluorescence decay-time and fiber Bragg grating temperature and strain sensing," Advanced Photonic Sensors and Applications II, Eds. Anand K. Asundi et al., Proceedings of SPIE vol. 4596, pp. 90-96, 2001.
Guan, Bai-Ou et al., "Cladding mode effect in superstructure fiber Bragg gratings and its applications in simultaneous strain and temperature measurement," Optical Fiber Communication Conference and Exhibit (OFC-2001), 2001, vol. 3, pp. WDD79-1-WDD79-3.
Guan, Bai-Ou et al., "Simultaneous strain and temperature measurement using a single fibre Bragg grating," Electronics Letters, Jun. 8, 2000, vol. 36, No. 12, pp. 1018-1019.
Guan, Bai-Ou et al., "Simultaneous Strain and Temperature Measurement Using a Superstructure Fiber Bragg Grating," IEEE Photonics Technology Letters, vol. 12, No. 6, pp. 675-677, Jun. 2000.
Guo, Tuan et al., "Temperature-Insensitive Fiber Bragg Grating Force Sensor via a Bandwidth Modulation and Optical-Power Detection Technique," Journal of Lightwave Technology, vol. 24, No. 10, pp. 3797-3802, Oct. 2006.
Gwandu, B.A.L. and W. Zhang, "Tailoring the temperature responsivity of fibre Bragg gratings," Proceedings of IEEE Sensors, Oct. 24-27, 2004, vol. 3, pp. 1430-1433.
Gwandu, B.A.L. et al., "Simultaneous Measurement of Strain, Temperature and Curvature Using a Sampled Fibre Bragg Grating," 15th Optical Fiber Sensors Conference (OFS 2002) Technical Digest, May 6-10, 2002, vol. 1, pp. 79-82.
Han, Kyung Jun et al., "Simultaneous Measurement of Strain and Temperature Incorporating a Long-Period Fiber Grating Inscribed on a Polarization-Maintaining Fiber," IEEE Photonics Technology Letters, vol. 16, No. 9, pp. 2114-2116, Sep. 2004.
Han, Young-Geun and Sang Bae Lee, "Simultaneous measurement of temperature and strain using dual long-period fiber gratings with controlled temperature and strain sensitivities," Optics Express, vol. 11, No. 5, pp. 476-481, Mar. 10, 2003.
Haran, Frank M. et al., "Rapid Communication: A strain-isolated fibre Bragg grating sensor for temperature compensation of fibre Bragg grating strain sensors," Measurement Science and Technology, vol. 9, pp. 1163-1166, 1998.
Harrington, James A., "Infrared Fiber Optics," 13 pages, posted online Jul. 8, 2004, Internet: http://irfibers.rutgers.edu/pdf_files/ir_fiber_review.pdf.
Hasegawa, Junichi and Kazutaka Nara, "Ultra-Low-Loss Athermal AWG Module with a Large Number of Channels," Furukawa Review, No. 26, pp. 1-4, 2004.
Hitz, Breck, "Birefringent Fiber Enhances Fiber Optic Strain Sensor," Photonics Spectra, Jan. 2007, pp. 30, 32, and 34.
Hitz, Breck, "Bragg Gratings Enable Efficient Phosphate Glass Fiber Lasers," Applied Physics Letters, Sep. 4, 2006, vol. 101127, pp. 1-3, Internet: http://www.photonics.com/printerFriendly.aspx?ArticleID=27529andPublication=5.
Hitz, Breck, "Wrinkles improve fiber optic strain sensor," Photonics Technology News, Jan. 2007, 3 Pages.
James, S.W. et al., "Simultaneous independent temperature and strain measurement using in-fibre Bragg grating sensors," Electronic Letters, vol. 32, No. 12, pp. 1133-1134, Jun. 6, 1996.
Jewell, John M., "Thermooptic Coefficients of Soda-Lime-Silica Glasses," Journal of the American Ceramic Society, vol. 76, Issue 7, pp. 1855-1856, Jul. 1993.
Jung, Jaehoon et al., "Simultaneous measurement of strain and temperature by use of a single-fiber Bragg grating and an erbium-doped fiber amplifier," Applied Optics, vol. 38, No. 13, pp. 2749-2751, May 1, 1999.
Jung, Jaehoon et al., "Simultaneous measurement of strain and temperature using a single fiber Brag grating written in an erbium: ytterblum-doped fiber," Summaries of papers presented at the Conference on Lasers and Electro-Optics (CLEO'99), May 23-28, 1999, p. 386.
Kaczmarek, Cesary et al., "Fiber Bragg Grating Differential Strain Sensor," 7th International Conference, "The Experience of Designing and Application of CAD Systems in Microelectronics" (CADSM'2003), Feb. 18-22, 2003, Lviv-Slaske, Ukraine, pp. 172-174.
Kalinowski, H.J. et al., "Characterisation of Bragg Gratings written in High Birefringence Fibre Optic for Sensor Applications," posted online May 2005, 4 pages, Internet: http://www.cpgei.cefetpr.br/~hypolito/artigos/2002-MumbaiHiBi.pdf.
Kalli, K. et al., Abstract of "Development of an electrically tuneable Bragg grating filter in polymer optical fibre operating at 1.55 µm," Measurement Science and Technology, vol. 18, p. 3155, 2007.
Kalli, Kyriacos et al., "Annealing and temperature coefficient study of type IA fibre Bragg gratings inscribed under strain and no strain—Implications to optical fibre component reliability," Proceedings of SPIE, Reliability of Optical Fiber Components, Devices, Systems, and Networks III, eds. Hans G. Limberger et al., vol. 6193, pp. 61930L-1 through 61930L-12, 2006.
Kalli, Kyriacos et al., "Impact of hydrogenation conditions on the temperature and strain coefficients of type 1 and type1a dual grating sensors," 17th International Conference on Optical Fibre Sensors, Eds. Marc Voet et al., Proceedings of SPIE, vol. 5855, pp. 892-895, 2005.
Kalli, Kyriacos et al., "Possible approach for the simultaneous measurement of temperature and strain via first and second order diffraction from Bragg grating sensors," SPIE vol. 2507, pp. 190-198, 1995.
Kalli, Kyriacos et al., "Tailoring the temperature and strain coefficients of Type I and Type IA dual grating sensors—the impact of hydrogenation conditions," Measurement Science and Technology, vol. 16, pp. 1-6, Mar. 10, 2005.
Kalli, Kyriacos et al., "The impact of hydrogenation conditions on the temperature and strain discrimination of Type I and Type IA Bragg grating sensors," Proceedings of SPIE, Optical Sensing II, Eds. Brian Culshaw et al., vol. 6189, pp. 61891T-1 through 61891T-8, 2006.
Kanellopoulos, Sotiris E. et al., "Simultaneous strain and temperature sensing with photogenerated in-fiber gratings," Optics Letters, vol. 20, No. 3, pp. 333-335, Feb. 1, 1995.
Kang, Hyun-Kyu et al., "Simultaneous Measurement of Strain and Temperature of Structures Using Fiber Optic Sensor," Journal of Intelligent Material Systems and Structures, vol. 12, pp. 277-281, Apr. 2001.
Keil, N. et al., Abstract of "Athermal polarisation-independent arrayed-waveguide grating (AWG) multiplexer using an all-polymer approach," Applied Physics, 2001, vol. B 73, No. 5-6, p. 619.
Kigre, Inc., Data Sheet for Glass Laser Rods, pp. 1-4, posted online Mar. 22, 2006, Internet: http://www.kigre.com/files/q98data.pdf.
Kigre, Inc., Data Sheet for Glass QE-7S Erbium-Doped Phosphate Laser Glass, 2 pages, 1989, Internet: http://www.kigre.com/files/qe7s.pdf.
Kim, Duk-Jun et al., "Thermal behavior of arrayed-waveguide grating made of silica/polymer hybrid waveguide," Electronics and Telecommunications Research Institute (ETRI) Journal, vol. 26, No. 6, pp. 661-664, Dec. 2004; Internet: etrij.etri.re.kr/Cyber/servlet/GetFile?fileid=SPF-1119246664089.
Kim, Sungchul et al., "Temperature-independent strain sensor using a chirped Bragg grating partially embedded in a glass tube," 12th Annual Meeting IEEE Lasers and Electro-Optics Society (LEOS'99), Nov. 8-11, 1999, vol. 2, pp. 878-879.
Koike, Akio and Naoki Sugimoto, Albert, J. et al., "Temperature Dependences of Optical Path Length in Inorganic Glasses," Reports of the Research Laboratory, Asahi Glass Co., Ltd., vol. 56, pp. 1-6, 2006.
Kojima, Seiji et al., "Embedding type strain sensors using small-diameter fiber Bragg grating to composite laminate structures," Hitachi Cable Review, No. 23, pp. 11-15, Aug. 2004.
Koyamada, Yahei et al., "Novel Fiber-Optic Distributed Strain and Temperature Sensor with Very High Resolution," IEICE Transactions on Communications, vol. E89-B, No. 5, pp. 1722-1725, May 2006, IEICE Communications Society, Japan.

(56) References Cited

OTHER PUBLICATIONS

Lee, E.T.Y. and E.R.M. Taylor, "Compositional effects on the optical and thermal properties of potassium aluminophosphate glasses," Optical Materials, vol. 27, Issue 2, Nov. 2004, pp. 323-330.

Lee, E.T.Y. and E.R.M. Taylor, Abstract of "Compositional Effects on the Thermo-optic Coefficients of Barium Borophosphate Glasses," in Fiber Lasers: Technology, Systems, and Applications, Eds. Michael J. F. Digonnet et al., International Society for Optical Engineering, Bellingham, Washington, 2004, Proceedings of SPIE, vol. 5350, p. 147.

Lee, E.T.Y. and E.R.M. Taylor, Abstract of "Compositional effects on the thermo-optic coefficients of potassium aluminophosphate glasses," 2003, 1 Page. Internet: http://en.scientificcommons.org/export/ris/16161764.

Lee, E.T.Y. and E.R.M. Taylor, Abstract of "Optical and thermal properties of binary calcium phosphate and barium phosphate glasses," Optical Materials, vol. 28, Issue 3, p. 200, Feb. 2006; available online Feb. 8, 2005.

Lee, E.T.Y. and E.R.M. Taylor, Abstract of "Two-die assembly for the extrusion of glasses with dissimilar thermal properties for fibre optic preforms," Journal of Materials Processing Technology, Apr. 12, 2007, vol. 184, Issues 1-3, p. 325; available online Dec. 29, 2006.

Lee, E.T.Y. and E.R.M. Taylor, Conclusion of Chapter 5, Study of the Optical and Thermal Properties of Phosphate Glasses, in Trends in Optical Materials Research, Ed. Owen G. Gardens, Nova Science Publishers, Inc., 2007, pp. 180-181.

Lee, Eric Tong Yih, "Development and characterization of phosphate glasses for athermalisation," Ph.D. Dissertation, University of Southampton Optoelectronics Research Centre, Jun. 2004, 258 pages.

Leick, L. et al., Athermal AWGs for colourless WDM-PON with −40° C. to +70° C. and underwater operation, 2006 National Fiber Optic Engineers Conference and Optical Fiber Communications Conference 2006, Mar. 5-10, 2006, pp. 1-3.

Li, Hongxia et al., "Thermal sensitivity of tellurite and germanate optical fibers," Optics Express, vol. 15, No. 14, pp. 8857-8863, Jul. 9, 2007.

Lim, Jirapong et al. "Strain and Temperature Sensors Using Multimode Optical Fiber Bragg Gratings and Correlation Signal Processing," IEEE Transactions on Instrumentation and Measurement, vol. 51, No. 4, pp. 622-627, Aug. 2002.

Lima, M.J.N. et al., "Comparison of the Temperature Dependence of Different Types of Bragg Gratings," Microwave and Optical Technology Letters, vol. 45, No. 4, pp. 305-307, May 20, 2005.

Liu, Y. et al., Summary of "Polymer fiber Bragg gratings tunable dispersion compensation," OFC/NFOEC Optical Fiber Communication Conference, Mar. 6-11, 2005, vol. 3, 1 page.

Liu, Y. et al., "Abnormal spectral evolution of fiber Bragg gratings in hydrogenated fibers," Optics Letters, vol. 27, No. 8, pp. 586-588, Apr. 15, 2002.

Mahmoud, M. et al., "Modeling and analysis on the thermal tuning of fiber Bragg gratings for optical communications applications", 3rd International Symposium on Communication Systems, Networks and DSP, Jul. 15-17, 2002, Stafford, U.K., pp. 86-89.

Mandal, Jharna et al., "Bragg grating tuned fiber laser system for measurement of wider range temperature and strain," Optics Communications, vol. 244, pp. 111-121, 2005.

Measures, Raymond M., "Fiber Optic Strain Sensing," in Fiber Optic Smart Structures, Ed. Eric Udd, Apr. 1995, Wiley, pp. 208-209.

Micron Optics, Inc., "Fiber Bragg Grating Strain Gage Temperature Compensation," 4 pages. Rev. A Oct. 2004; Internet: http://wwvv.micronoptics.com/.

Micron Optics, Inc., "os310 Strain Gage Temperature Compensation," 3 pages. Rev. C, Jan. 2007; Internet: http://www.micronoptics.com/.

Nee, Soe-Mie F. et al., Abstract of "Optical and surface properties of oxyfluoride glass," Proceedings of SPIE, vol. 4102, p. 122, 2000.

Nippon Telegraph and Telephone Corporation, "Low-loss and Flatpassband Athermal AWG Multiplexer," 2008, 1 Page, Internet: http://www.phlab.ecl.ntt.co.jp/eng/theme/2008/NTT-PH-E-03-03.pdf.

Oh, S.T. et al., "Discrimination of temperature and strain with a single FBG based on the birefringence effect," Optics Express, vol. 12, No. 4, pp. 724-729, Feb. 23, 2004.

Oz Optics, Data Sheet "Fiber Optic Distributed Brillouin Sensors," Oct. 20, 2006, 5 Pages; Internet: www.ozoptics.com.

Oz Optics, Data Sheet "Fiber Optic Distributed Brillouin Sensors," Sep. 22, 2006, 4 Pages; Internet: www.ozoptics.com.

Pal, Suchandan et al., "Bragg grating performance in Er—Sn-doped germanosilicate fiber for simultaneous measurement of wide range temperature (to 500° C.) and strain," Review of Scientific Instruments, vol. 74, No. 11, pp. 4858-4862, Nov. 2003.

Pal, Suchandan et al., "Simultaneous Measurement of Strain (to 2000 µe) and Temperature (to 600 C) Using a Combined Sb—Er—Ge-Codoped Fiber-Fluorescence and Grating-Based Technique," IEEE Sensors Journal, vol. 5, No. 6, pp. 1462-1468, Dec. 2005.

Pal, Suchandan et al., "Strain-independent temperature measurement using a type-I and type-IIA optical fiber Bragg grating combination," Review of Scientific Instruments, vol. 75, No. 5, pp. 1327-1331, May 2004.

Patrick, H.J. et al., "Hybrid Fiber Bragg Grating/Long Period Fiber Grating Sensor for Strain/Temperature Discrimination," IEEE Photonics Technology Letters, vol. 8, No. 9, pp. 1223-1225, Sep. 1996.

Pilla, V. et al., "Thermal-lens study of thermo-optical properties of tellurite glasses," 4th Brazilian MRS Meeting, Journal of Materials Science, vol. 42, pp. 2304-2308, 2007.

Posey Jr., Ralph and Sandeep T. Vohra, "An Eight-Channel Fiber-Optic Bragg Grating and Stimulated Brillouin Sensor System for Simultaneous Temperature and Strain Measurements," IEEE Photonics Technology Letters, vol. 11, No. 12, pp. 1461-1643, Dec. 1999.

Rao, Y.J. et al., "Temperature-Strain Discrimination Using a Wavelength-Division-Multiplexed Chirped in-Fibre-Bragg-Grating/Extrinsic Fabry-Perot Sensor system," 15th Optical Fiber Sensors Conference Technical Digest, 2002 (OFS 2002), May 6-10, 2002, vol. 1, pp. 207-210.

Rego, G. et al., "Simultaneous measurement of temperature and strain based on arc-induced long-period fibre gratings," Electronics Letters, Jan. 20, 2005, vol. 41 No. 2, pp. 60-62.

Saad, Mohammed and Jean-Sebastien Tasse, "Fluoride glasses draw fiber into the mid-infrared," 3 Pages, 2007, Internet: http://www.laserfocusworld.com/articles/292400.

Sanghera, Jasbinder S. and Ishwar D. Aggarwal, Infrared Fiber Optics, CRC Press, 1998, pp. 76-85.

Seneschal, Karine et al., Abstract of "Alkaline-free phosphate glasses for ultra compact optical fiber amplifiers at 1.5 µm," Letters to the Editor, Journal of Non-Crystalline Solids, Posted online Jul. 9, 2003; Published in vol. 324, Issue 1-2, Aug. 15, 2003, p. 179.

Shu, X. et al., "Fiber grating type dependence of temperature and strain coefficients and application to simultaneous temperature and strain measurement," 15th Optical Fiber Sensors Conference (OFS 2002) Technical Digest, May 6-10, 2002, vol. 1, pp. 83-86.

Shu, Xuewen et al., "Dependence of temperature and strain coefficients on fiber grating type and its application to simultaneous temperature and strain measurement," Optics Letters, vol. 27, No. 9, pp. 701-703, May 1, 2002.

Shu, Xuewen et al., "Effectively simultaneous temperature and strain measurement utilising a dual-grating sensor formed by Type IA and Type IIA FBGs," p. 1, 2002.

Shu, Xuewen et al., "High-Temperature Sensitivity of Long-Period Gratings in B—Ge Codoped Fiber," IEEE Photonics Technology Letters, vol. 13, No. 8, pp. 818-820, Aug. 2001.

Shu, Xuewen et al., "Sensitivity Characteristics of Long-Period Fiber Gratings," Journal of Lightwave Technology, vol. 20, No. 2, pp. 255-266, Feb. 2002.

Shu, Xuewen et al., "Use of dual-grating sensors formed by different types of fiber Bragg gratings for simultaneous temperature and strain measurements," Applied Optics, vol. 43, No. 10, pp. 2006-2012, Apr. 1, 2004.

Silva-Lopez, Manuel et al., "Strain and temperature sensitivity of a single-mode polymer optical fiber," Optics Letters, vol. 30, No. 23, pp. 3129-3131, Dec. 1, 2005.

Simpson, George et al., "An idealised method for the fabrication of temperature invariant Ia-I strain sensors," 16th International confer-

(56) References Cited

OTHER PUBLICATIONS ence on Optical Fiber Sensors (OFS-16), Oct. 13-17, 2003, Post Deadline Session, pp. 14-17, Nara, Japan.

Simpson, George et al., "Blank beam fabrication of regenerated type IA gratings," Measurement Science and Technology, vol. 15, pp. 1665-1669, 2004, IOP Publishing, U.K.

Simpson, George et al., "Formation of type IA fibre Bragg gratings in germanosilicate optical fibre," Electronic Letters, vol. 40, No. 3, pp. 163-164, Feb. 5, 2004.

Simpson, George et al., "Type 1A fibre Bragg grating photosensitivity and the development of optimum temperature invariant type I-type IA strain sensors," Proceedings of SPIE, vol. 5459, pp. 118-127, 2004.

Sivanesan, Ponniah et al., "Optimal wavelength pair selection and accuracy analysis of dual fiber grating sensors for simultaneously measuring strain and temperature," Optical Engineering, vol. 41, Issue 10, pp. 2456-2463, Oct. 2002.

Sivanesan, Ponniah, "Optical Fiber Sensor for Simultaneous Measurement of Distributed Strain and Temperature," Ph.D. Dissertation, University of Maryland College Park, Department of Physics, pp. 1-51, 2002.

Sorensen, H.R. et al., "Control of the wavelength dependent thermooptic coefficients in structured fibres," Optics Express, vol. 14, No. 14, pp. 6428-6433, Jul. 10, 2006.

Tran, Thi Van Anh et al., "Performance Enhancement of Long-Distance Simultaneous Measurement of Strain and Temperature Based on a Fiber Raman Laser with an Etched FBG," IEEE Photonics Technology Letters, vol. 17, No. 9, pp. 1920-1922, Sep. 2005.

Trpkovski, S. et al., "Dual temperature and strain sensor using a combined fiber Bragg grating and fluorescence intensity ratio technique in Er3+-doped fiber," Review of Scientific Instruments, vol. 74, No. 5, pp. 2880-2885, May 2003.

Udd, Eric et al., "Distributed multiaxis fiber grating strain sensor applications for bridges," Fiber Optic Sensors for Construction Materials, Pennsylvania: Technomic, 1998, pp. 168-180. Internet: http://www.bluerr.com/27.PDF.

U.S. Appl. No. 60/019,038, Specification filed May 20, 1996, pp. 1-16.

Vertut, Jean et al., Robot Technology: Teleoperation and Robotics Evolution and Development, 1986, vol. 3A, 332 pages, English translation Prentice-Hall, Inc., Inglewood Cliffs, NJ, USA.

Wade, S.A. et al., "Fiber optic sensor for dual measurement of temperature and strain using a combined fluorescence lifetime decay and fiber Bragg grating technique," Review of Scientific Instruments, vol. 72, No. 8, pp. 3186-3190, Aug. 2001.

Wikszak, E. et al., Abstract of "Femtosecond written fiber Bragg Grating in non-photosensitive rare-earth-doped fiber," Conference on Lasers and Electro-Optics and 2006 Quantum Electronics and Laser Science Conference (CLEO/QELS 2006), May 21, 26, 2006, Long Beach, California, Page 1.

Wong, Allan C. L. et al., "Multiplexed fibre Fizeau interferometer and fibre Bragg grating sensor system for simultaneous measurement of quasi-static strain and temperature using discrete wavelet transform," Measurement Science and Technology, 2006, pp. 384-392, vol. 17—Issue 2, Institute of Physics Publishing.

Wu, Meng-Chou and William H. Prosser, "Simultaneous temperature and strain sensing for cryogenic applications using dual-wavelength fiber Bragg gratings," SPIE, vol. 5191, pp. 208-213, Dec. 2003.

Xie, H. et al., "Temperature dependent properties of titanium oxide thin films by spectroscopic ellipsometry," SIMTech Technical Reports, vol. 9, No. 1, pp. 29-32, Jan.-Mar. 2008, Internet: http://www.simtech.a-star.edu.sg/Research/TechnicalReports/STR_V9_N1_CD_Version/STR_V9_N1_06_PMG.pdf.

Xu, M.G. et al., "Discrimination between strain and temperature effects using dual-wavelength fibre grating sensors," Electronic Letters, vol. 30, No. 13, pp. 1085-1087, Jun. 23, 1994.

Xu, M.G. et al., "Temperature-independent strain sensor using a chirped Bragg grating in a tapered optical fibre," Electronic Letters, vol. 31, No. 10, pp. 823-825, May 11, 1995.

Yamate, Tsutomu et al., "Thermally Insensitive Pressure Measurements up to 300 degree C Using Fiber Bragg Gratings Written onto Side Hole Single Mode Fiber," Proceedings of SPIE, vol. 4185, pp. 628-631, 2000, Internet: http://www.bluerr.com/papers/BRR-2000_SPIE_Vol4185_p628.pdf.

Yang, Bin et al., "Fibre Bragg Grating Sensor for Simultaneous Measurement of Strain and Temperature," Journal of Industrial Textiles, vol. 34, No. 2, pp. 97-115, Oct. 2004.

Ye, Winnie N. et al., "Athermal Designs," EMAT@MIT, 2007, 2 pages, Internet: http://photonics.mit.edu/Athermal.html.

Yu, Youlong et al., "Passive temperature compensation technique for fibre Bragg grating displacement sensor," Electronic Letters, vol. 35, No. 25, 2 pages, Dec. 9, 1999.

Zhang, L. et al., "Advances in UV-inscribed fiber grating optic sensor technologies," Proceedings of IEEE Sensors, Jun. 12-14, 2002, vol. 1, pp. 31-35.

Zhang, Lin et al., "Advanced optical sensing techniques using novel fibre gratings," Proceedings of 2002 IEEE/LEOS Workshop on Fibre and Optical Passive Components, Jun. 5-6, 2002, pp. 65-74.

Zhao, Chun-Liu et al., "Studies on Strain and Temperature Characteristics of a Slanted Multimode Fiber Bragg Grating and Its Application in Multiwavelength Fiber Raman Ring Laser," Journal of Lightwave Technology, vol. 24, No. 6, pp. 2394-2400, Jun. 2006.

Zhou, Yingwu et al, "Temperature and Stress Tuning Characteristics of Long-Period Gratings Imprinted in Panda Fiber," IEEE Photonics Technology Letters, vol. 15, No. 12, pp. 1728-1730, Dec. 2003.

Zhu, Yinian et al., "Temperature insensitive measurements of static displacements using a fiber Bragg grating," Optics Express, vol. 11, No. 16, pp. 1918-1924, Aug. 11, 2003.

Zhu, Yinian et al., "Temperature-Insensitive Fiber Bragg Grating Accelerometer," IEEE Photonics Technology Letters, vol. 15, No. 10, pp. 1437-1439, Oct. 2003.

\* cited by examiner

FIG. 5C1

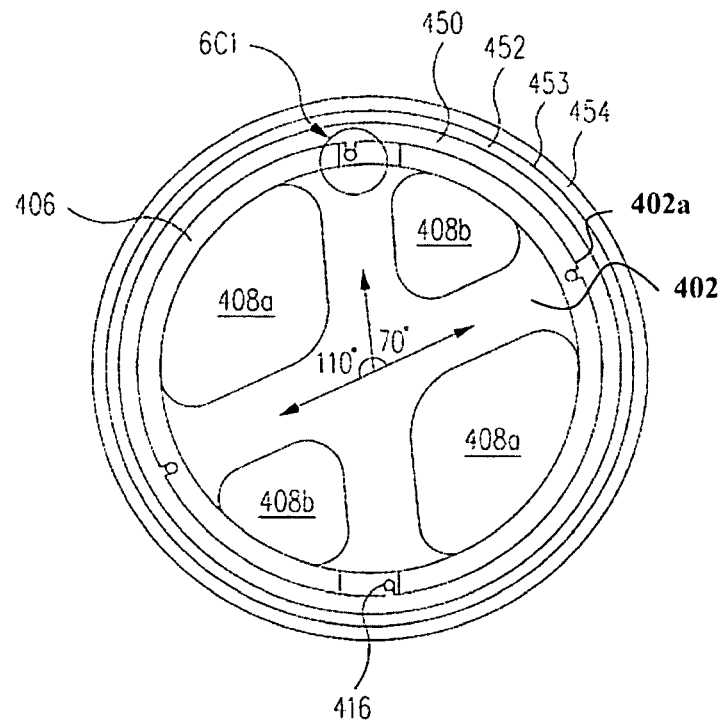
FIG. 6C
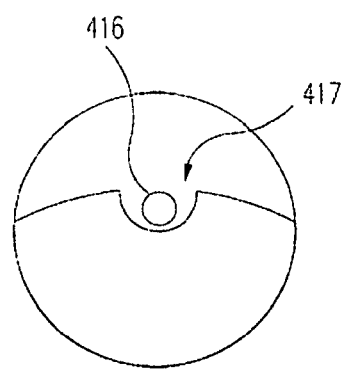
FIG. 6C1

FIG. 7B1

FORCE SENSOR TEMPERATURE COMPENSATION

CROSS-REFERENCE TO RELATED APPLICATIONS AND PATENTS

This application is a continuation-in-part of U.S. application Ser. No. 11/958,772, filed Dec. 18, 2007, which is incorporated by reference herein for all purposes.

This application is related to U.S. Provisional Application No. 60/755,108 filed Dec. 30, 2005, U.S. Provisional Application 60/755,157 filed Dec. 30, 2005, U.S. application Ser. No. 11/553,303 filed Oct. 26, 2006, U.S. patent application Ser. No. 11/537,241 filed Sep. 29, 2006, U.S. patent application Ser. No. 11/093,372 filed Mar. 30, 2005, and U.S. Pat. Nos. 6,936,042, 6,902,560, 6,879,880, 6,866,671, 6,817,974, 6,783,524, 6,676,684, 6,371,952, 6,331,181, and 5,807,377, the full disclosures of which are incorporated by reference herein for all purposes.

TECHNICAL FIELD

The present invention relates generally to surgical robot systems and, more particularly, to an improved system, apparatus, and method for sensing forces applied to a surgical instrument.

BACKGROUND

In robotically-assisted surgery, the surgeon typically operates a master controller to control the motion of surgical instruments at the surgical site from a location that may be remote from the patient (e.g., across the operating room, in a different room or a completely different building from the patient). The master controller usually includes one or more hand input devices, such as handheld wrist gimbals, joysticks, exoskeletal gloves, handpieces, or the like, which are operatively coupled to the surgical instruments through a controller with servo motors for articulating the instruments' position and orientation at the surgical site. The servo motors are typically part of an electromechanical device or surgical manipulator arm ("the slave") that includes a plurality of joints, linkages, etc., that are connected together to support and control the surgical instruments that have been introduced directly into an open surgical site or through trocar sleeves (cannulas) inserted through incisions into a body cavity, such as the patient's abdomen. There are available a variety of surgical instruments, such as tissue graspers, needle drivers, electrosurgical cautery probes, etc., to perform various functions for the surgeon, e.g., retracting tissue, holding or driving a needle, suturing, grasping a blood vessel, dissecting, cauterizing, coagulating tissue, etc. A surgeon may employ a large number of different surgical instruments/tools during a procedure.

This new surgical method through remote manipulation has created many new challenges. One such challenge is providing the surgeon with the ability to accurately "feel" the tissue that is being manipulated by the surgical instrument via the robotic manipulator. The surgeon must rely on visual indications of the forces applied by the instruments or sutures. It is desirable to sense the forces and torques applied to the tip of the instrument, such as an end effector (e.g., jaws, grasper, blades, etc.) of robotic minimally invasive surgical instruments, in order to feed the forces and torques back to the surgeon user through the system hand controls or by other means, such as visual display, vibrations, or audible tone. One device for this purpose from the laboratory of G. Hirzinger at DLR Institute of Robotics and Mechatronics is described in "Review of Fixtures for Low-Invasiveness Surgery" by F. Cepolina and R. C. Michelini, *Int'l Journal of Medical Robotics and Computer Assisted Surgery*, Vol. 1, Issue 1, page 58, the contents of which are incorporated by reference herein for all purposes. However, that design disadvantageously places a force sensor distal to (or outboard of) the wrist joints, thus requiring wires or optic fibers to be routed through the flexing wrist joint and also requiring the yaw and grip axes to be on separate pivot axes.

Another problem has been fitting and positioning the necessary wires, rods, or tubes for mechanical actuation of end effectors in as small a space as possible because relatively small instruments are typically desirable for performing surgery.

Furthermore, the temperature sensitivity of force sensors has caused problems with providing accurate force measurements.

What is needed, therefore, are improved telerobotic systems, surgical apparatus, and methods for remotely controlling surgical instruments at a surgical site on a patient. In particular, these systems and methods should be configured to provide accurate feedback of forces and torques to the surgeon to improve user awareness and control of the instruments.

SUMMARY

The present invention provides an apparatus, system, and method for improving force and torque feedback to and sensing by a surgeon performing a robotic surgery. In one embodiment, a force sensor includes a tube portion that includes a plurality of radial ribs and a strain gauge or gauges positioned over each of the plurality of radial ribs. A proximal part of the tube portion is coupled to a shaft of a surgical instrument that may be operably coupled to a manipulator arm of a robotic surgical system. A distal part of the tube portion is coupled to a wrist joint coupled to an end effector. The couplings may be direct or indirect with an intermediate mechanical component between the coupled parts.

Groups of strain gauges are positioned on or near a distal end of an instrument shaft proximal to (i.e., inboard of) a moveable wrist of a robotic surgical instrument via an apparatus that senses forces and torques at the distal tip of the instrument without errors due to changes in the configuration of the tip (such as with a moveable wrist) or steady state temperature variations.

The force sensor apparatus may be comprised of advantageous materials, such as high thermal diffusivity material and negative or differing thermo-optic coefficient optical fiber material, and/or include thermal shielding/heat spreading designs to provide accurate force signals even under asymmetric transient thermal loads that may occur in surgery.

Advantageously, the present invention improves the sensing and feedback of forces to the surgeon and substantially eliminates the problem of passing delicate wires, or optic fibers through the flexible wrist joint of the instrument. A force sensor apparatus may be manufactured, tested, and calibrated as a separate modular component and brought together with other components in the conventional instrument assembly process. The force sensor apparatus may also be manufactured as an integrated part of the instrument shaft. In addition, it is possible to choose a material for the sensor structural member different from the material of the instrument shaft whose design considerations may compromise the mechanical and/or thermal properties required for the sensor.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIG. 5C1 illustrates a magnified section labeled 5C1 in FIG. 5C.

FIG. 6C illustrates an end view of the force sensor apparatus of FIGS. 6A and 6B including radial ribs positioned in non-uniform angles, and FIG. 6C1 illustrates a magnified section labeled 6C1 in FIG. 6C, in accordance with another embodiment of the present invention.

FIG. 7B1 illustrates a magnified section labeled 7B1 in FIG. 7B, in accordance with another embodiment of the present invention.

Figure 1A:
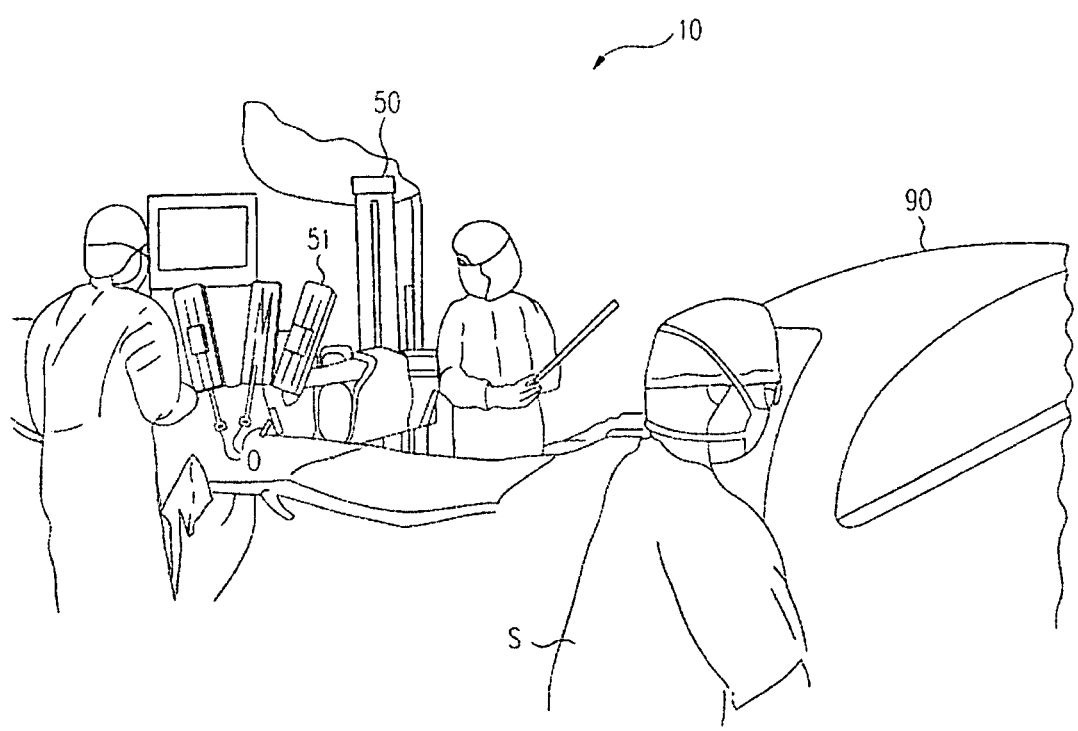
FIG. 1A is a perspective view of a robotic surgical system in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides a multi-component system, apparatus, and method for sensing forces applied to tissue while performing robotically-assisted surgical procedures on a patient, particularly including open surgical procedures, neurosurgical procedures, and minimally invasive procedures, such as laparoscopy, arthroscopy, thoracoscopy, and the like. The apparatus and method of the present invention are particularly useful as part of a telerobotic surgical system that allows the surgeon to manipulate the surgical instruments through a servomechanism from a location remote from the patient. To that end, the combined manipulator apparatus or slave and surgical instrument of the present invention will usually be driven by a master having the same degrees of freedom (e.g., 3 degrees of freedom for position and 3 degrees of freedom for orientation plus grip) to form a telepresence system with force reflection or other scalar force magnitude display. A description of a suitable slave-master system can be found in U.S. Pat. No. 6,574,355, the complete disclosure of which is incorporated herein by reference for all purposes.

Figure 1B:
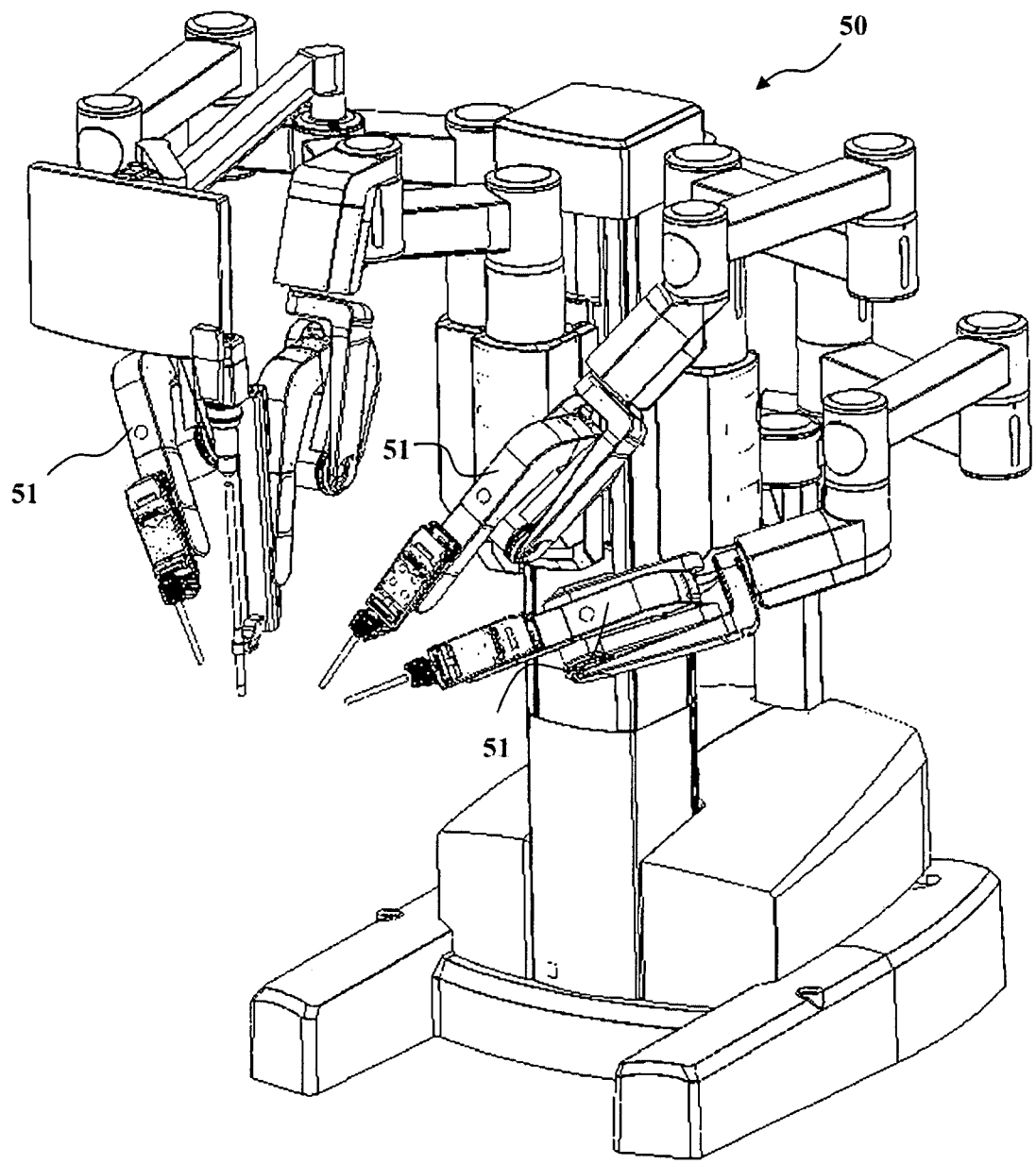
FIG. 1B is a perspective view of a robotic surgical arm cart system of the robotic surgical system in FIG. 1A in accordance with an embodiment of the present invention.
Figure 1C:
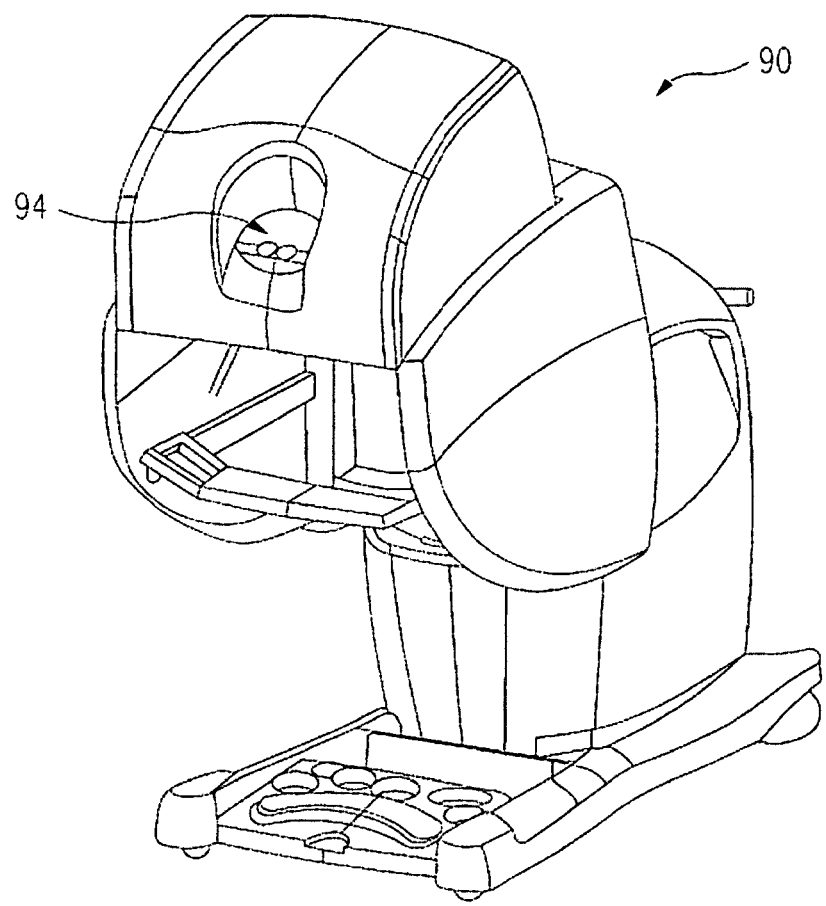
FIG. 1C is a front perspective view of a master console of the robotic surgical system in FIG. 1A in accordance with an embodiment of the present invention.

Referring to the drawings in detail, wherein like numerals indicate like elements, a robotic surgical system 10 is illustrated according to an embodiment of the present invention. As shown in FIGS. 1A through 1C, robotic system 10 generally includes one or more surgical manipulator assemblies 51 mounted to or near an operating table O and a master control assembly located at a surgeon's console 90 for allowing the surgeon S to view the surgical site and to control the manipulator assemblies 51. The system 10 will also include one or more viewing scope assemblies and a plurality of surgical instrument assemblies 54 (FIG. 2) adapted for being removably coupled to the manipulator assemblies 51 (discussed in more detail below). Robotic system 10 includes at least two manipulator assemblies 51 and preferably at least three manipulator assemblies 51. The exact number of manipulator assemblies 51 will depend on the surgical procedure and the space constraints within the operating room among other factors. As discussed in detail below, one of the assemblies 51 will typically operate a viewing scope assembly (e.g., in endoscopic procedures) for viewing the surgical site, while the other manipulator assemblies 51 operate surgical instruments 54 for performing various procedures on the patient.

The control assembly may be located at a surgeon's console 90 which is usually located in the same room as operating table O so that the surgeon may speak to his/her assistant(s) and directly monitor the operating procedure. However, it should be understood that the surgeon S can be located in a different room or a completely different building from the patient. The master control assembly generally includes a support, a monitor for displaying an image of the surgical site to the surgeon S, and one or more master(s) for controlling manipulator assemblies 51. Master(s) may include a variety of input devices, such as hand-held wrist gimbals, joysticks, gloves, trigger-guns, hand-operated controllers, voice recognition devices, or the like. Preferably, master(s) will be provided with the same degrees of freedom as the combined manipulator 51 and surgical instrument assemblies 54. In conjunction with the endoscopic view, this provides the surgeon with telepresence, the perception that the surgeon is immediately adjacent to and immersed in the surgical site, and intuitiveness, the perception that the master(s) are integral with the instruments 54 so that the surgeon has a strong sense of directly and intuitively controlling instruments 54 as if they are part of or held in his/her hands. Position, force, and tactile feedback sensors (not shown) may also be employed on instrument assemblies 54 to transmit position, force, and tactile sensations from the surgical instrument back to the surgeon's hands, ears, or eyes as he/she operates the telerobotic system. One suitable system and method for providing telepresence to the operator is described in U.S. Pat. No. 6,574,355, which has previously been incorporated herein by reference.

The monitor 94 (FIG. 1C) will be suitably coupled to the viewing scope assembly such that an image of the surgical site is provided adjacent the surgeon's hands on the surgeon console. Preferably, monitor 94 will display an image that is oriented so that the surgeon feels that he or she is actually looking directly down onto the operating site. To that end, an image of the surgical instruments 54 appears to be located substantially where the operator's hands are located. In addition, the real-time image is a stereo image such that the operator can manipulate the end effector via the hand control as if viewing the workspace in substantially true presence. The image simulates the viewpoint or orientation of an operator who is physically manipulating the surgical instruments 54.

A servo control is provided for transferring the mechanical motion of masters to manipulator assemblies 51. The servo control may be separate from, or integral with, manipulator assemblies 51. The servo control will usually provide force and torque feedback from the surgical instruments 51 to the hand-operated masters. In addition, the servo control may include a safety monitoring controller (not shown) to safely halt system operation, or at least inhibit all robot motion, in response to recognized undesirable conditions (e.g., exertion of excessive force on the patient, mismatched encoder readings, etc.). The servo control preferably has a servo bandwidth with a 3 dB cut off frequency of at least 10 Hz so that the system can quickly and accurately respond to the rapid hand motions used by the surgeon and yet to filter out undesirable surgeon hand tremors. To operate effectively with this system, manipulator assemblies 51 have a relatively low inertia, and the drive motors have relatively low ratio gear or pulley couplings. Any suitable conventional or specialized servo control may be used in the practice of the present invention, with those incorporating force and torque feedback being particularly preferred for telepresence operation of the system.

Figure 2:
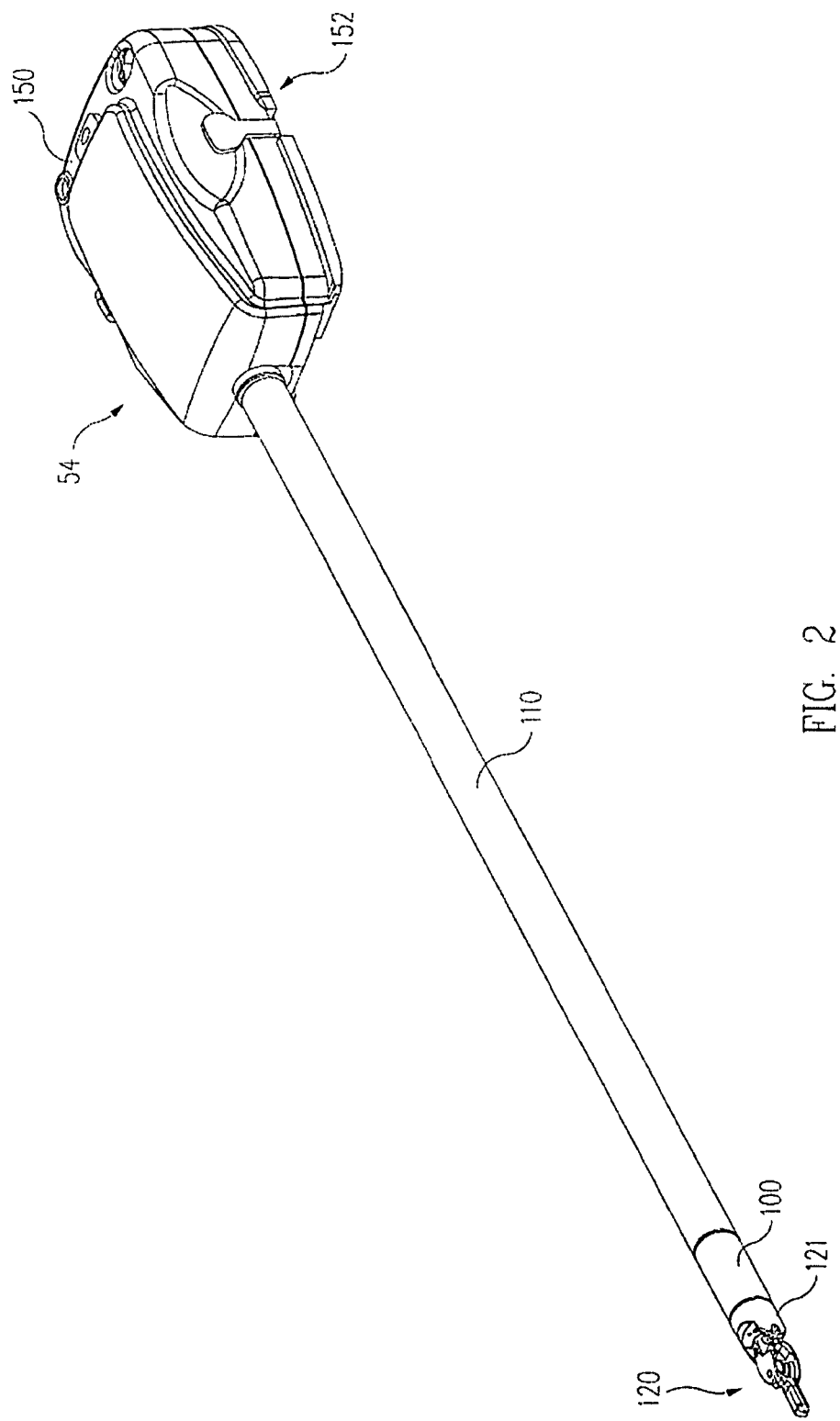
FIG. 2 is a perspective view of a surgical instrument including a force sensor apparatus operably coupled proximal (or inboard) to a wrist joint in accordance with an embodiment of the present invention.

Referring to FIG. 2, a perspective view is shown of a surgical instrument 54 including a force sensor apparatus 100 operably coupled to a distal end of a rigid shaft 110 and proximal to a wrist joint 121 in accordance with an embodiment of the present invention. An end portion 120, such as a surgical end effector, is coupled to force sensor apparatus 100 via the wrist joint 121. A housing 150 is operably coupled to a proximal end of the rigid shaft 110 and includes an interface 152 which mechanically and electrically couples instrument 54 to the manipulator 51.

Figure 3A:
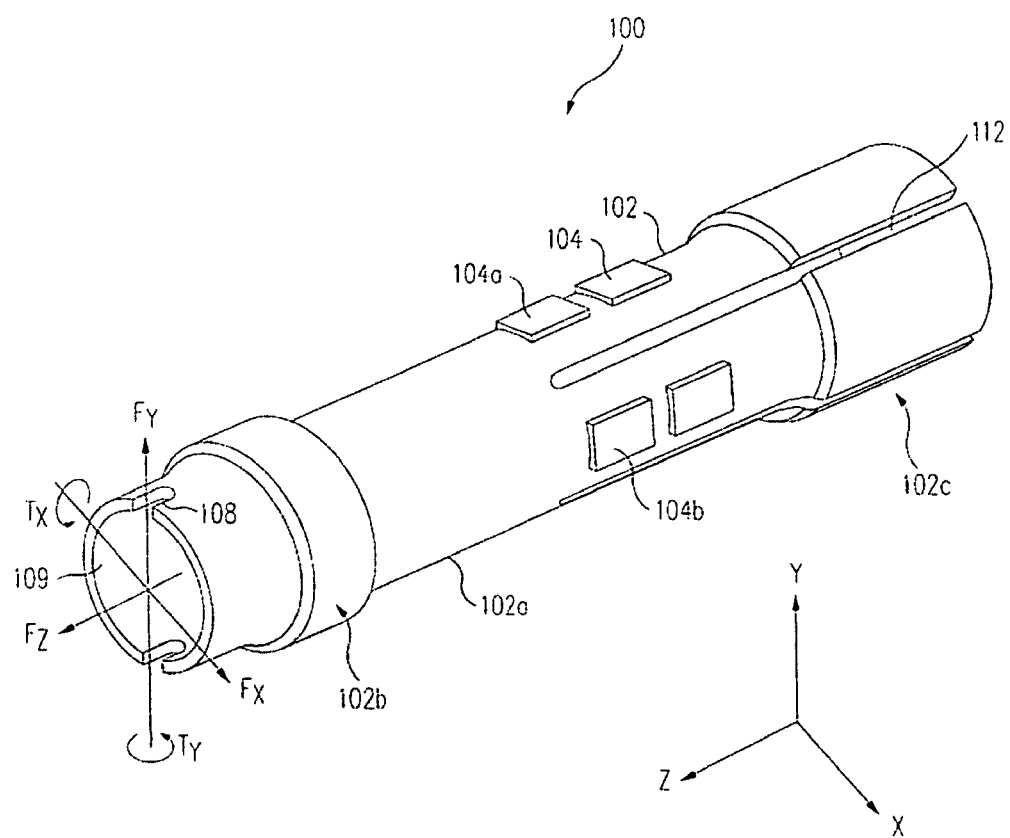
FIG. 3A is a perspective view of a force sensor apparatus.
Figure 3B:
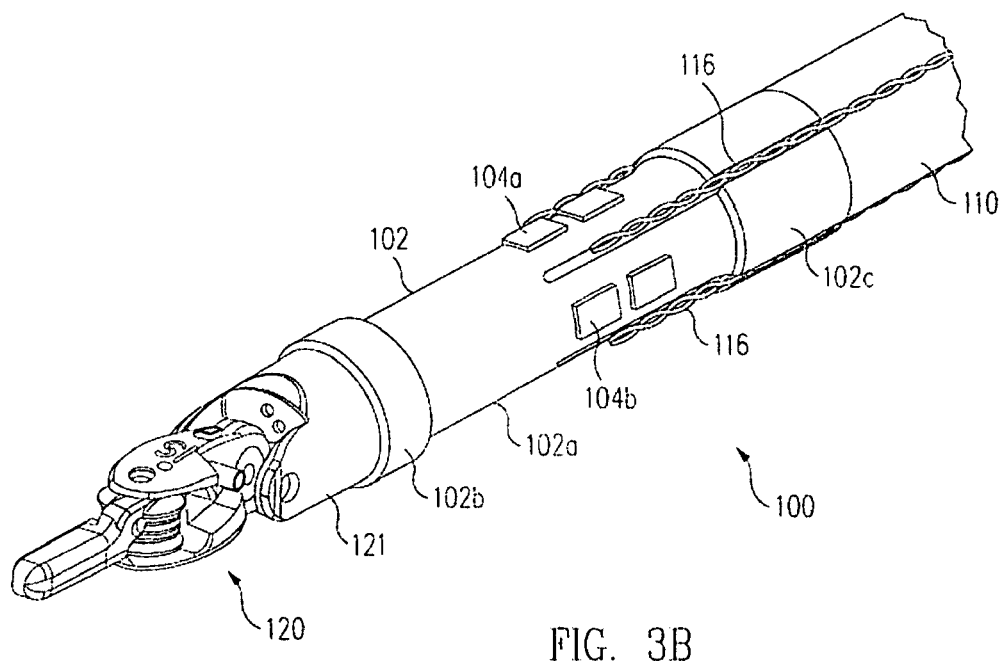
FIG. 3B illustrates the force sensor of FIG. 3A operably coupled to a shaft and end portion of a surgical instrument.
Figure 3C:
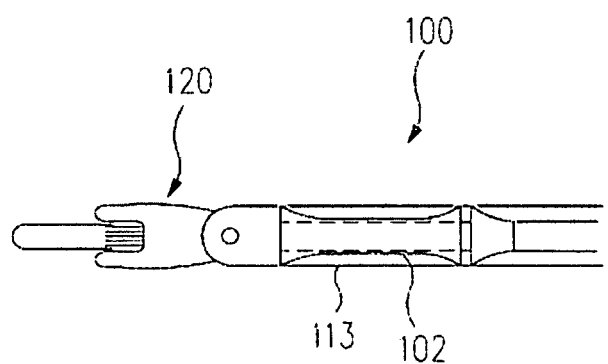
FIG. 3C illustrates the force sensor of FIG. 3A with a protective cover over a portion of the force sensor.

Referring now to FIGS. 3A-3C in conjunction with FIGS. 1A-1C and 2, an improved apparatus, system, and method for sensing and feedback of forces and/or torques to the surgeon will be described. FIG. 3A shows a perspective view of force sensor apparatus 100 including in one embodiment a tube 102 including a number (e.g., 3, 4, 6, or 8) of strain gauges 104 (e.g., 104a and 104b) mounted to a surface of tube 102 and oriented axially (parallel to the lengthwise axis z of the tube). FIG. 3B shows the force sensor apparatus 100 of FIG. 3A operably coupled to a shaft 110 and end portion 120 of a surgical instrument. FIG. 3C shows a cross-section view of force sensor apparatus 100 including a cover or sleeve 113 over tube 102.

Force sensor apparatus 100 is a separately manufacturable module or part adapted for incorporation as part of the shaft 110 of surgical instrument 54 at a prescribed distance from the tip where there may be an articulated wrist with specialized jaws, cutting devices, or other end portion 120. In one example, tube 102 may be made of a sufficiently strong material and may be spool shaped, including end portions 102b, 102c with a depressed portion 102a therebetween that is smaller in diameter than end portions 102b, 102c. Strain gauges 104 may be mounted on the surface of depressed portion 102a. Proximal tube portion 102c operably couples to the shaft 110 of surgical instrument 54 and distal tube portion 102b operably couples to a wrist joint 121. In one example, the diameter of the completed force sensor apparatus matches the diameter of the instrument shaft, thus allowing the entire assembly of the instrument (including the coupled force sensor apparatus) to pass through a cannula or a seal without added friction or snagging.

Force sensor apparatus 100 includes a through passage 109 for end portion actuation cables or rods. End features 108 of end portion 102b insure secure mounting and angular alignment to the main instrument shaft or the wrist/jaw/other end portion sub-assembly of the instrument. Wire leads or optic fibers 116 (e.g., shielded twisted pairs, coax, or fiber) from the strain gauges 104 may be inlaid into grooves 112 in the tube 102 and matching grooves in the shaft 110 of the surgical instrument 54. The wire leads or optic fibers 116 may then be embedded in an adhesive bonding or potting compound such as epoxy.

In one embodiment, as illustrated in FIG. 3C, cover 113 is positioned over and encapsulates the mounted strain gauges 104 and other circuit elements on the surface of the tube 102, thereby providing mechanical and/or electrical protection of the sensors. In one example, cover 113 is a mechanically protective woven sleeve potted on depressed portion 102a and is comprised of a woven resin impregnated fiberglass or metal braid electrical shielding.

As disclosed in U.S. patent application Ser. No. 11/537,241, filed Sep. 29, 2006, the contents of which have been previously incorporated by reference, strain gauges 104 may be spaced in a ring at intervals around the circumference of the tube 102 (e.g., 3 gauges at 120 degrees, 4 gauges at 90 degrees, or 4 gauges at 70 degrees and 110 degrees or other pairs of supplementary angles). The signals from the sensors are combined arithmetically in various sums and differences to obtain measures of transverse forces $F_x$ and $F_y$ (FIG. 3A) exerted upon the instrument tip and to reject axial force $F_z$ and the torques $T_x$ and $T_y$ about the two axes perpendicular to the shaft axis (i.e., axes x and y). The measurement of the forces is made independent of the orientation and effective lever arm length of an articulated wrist mechanism 121 at the distal end of the instrument when two axially separated sets or rings of gauges are utilized and their signals are subtracted. Forces exerted against end portion 120 are detected by the force sensing elements via an interrogator 334 (FIG. 5E), which may be operably coupled to the servo control or to a processor 340 (FIG. 5E) for notifying the surgeon of these forces (e.g., via master(s) or a display). It is understood that by adding a second ring of similarly oriented gauges (e.g., two sets of 3 gauges or two sets of 4 gauges) at a different lengthwise axial position on the tube, additional load-induced bending moment information may be obtained, and dependence of the transverse force data Fx, Fy on instrument wrist length, orientation, and resulting jaw distance may be eliminated.

In one example, various strain gauge types may be used, including but not limited to conventional foil type resistance gauges, semiconductor gauges, optic fiber type gauges using Bragg grating or Fabry-Perot technology, or others, such as strain sensing surface acoustic wave (SAW) devices. Optic fiber Bragg grating (FBG) gauges may be advantageous in that two sensing elements may be located along one fiber at a known separation, thereby only requiring the provision of four fibers along the instrument shaft for eight gauges.

Both fiber technologies require an interrogator unit 334 that decodes the optically encoded strain information into electrical signals compatible with the computer control hardware 340 or display means of the robotic surgical system. A processor may then be used to calculate forces according to the signals from the strain gauges/sensors.

Additionally, there may be co-mounted unstrained gauges or Poisson strained gauges oriented in the circumferential direction adjacent to each axial gauge and incorporated in the bridge completion circuits to eliminate temperature effects. The strain gauge bridge circuits are completed in a manner to give the best signal for bending loads due to the lateral forces ($F_x$ and $F_y$) exerted on the instrument tip jaws.

For resistive foil or semiconductor strain gauges, active components such as bare die op-amps and passive components such as secondary resistors or capacitors may be attached adjacent to the strain gauges connected by bond wires or thick film circuit traces in the manner of hybrid circuits to amplify, filter, and/or modulate the gauge output signals to reject noise sources. Such components are not needed for fiber optic gauges.

Housing 150 operably interfaces with a robotic manipulator arm 51, in one embodiment via a sterile adaptor interface 152 (FIG. 2). Applicable housings, sterile adaptor interfaces, and manipulator arms are disclosed in U.S. patent application Ser. No. 11/314,040 filed on Dec. 20, 2005, and U.S. application Ser. No. 11/613,800 filed on Dec. 20, 2006, the full disclosures of which are incorporated by reference herein for all purposes. Examples of applicable shafts, end portions, housings, sterile adaptors, and manipulator arms are manufactured by Intuitive Surgical, Inc. of Sunnyvale, Calif.

In a preferred configuration, end portion 120 has a range of motion that includes pitch and yaw motion about the x- and y-axes and rotation about the z-axis (axes shown in FIG. 3A). These motions as well as actuation of an end effector are provided via cables in housing 150 and cables and/or rods running through shaft 110 and into housing 150 that transfer motion from the manipulator arm 51. Embodiments of drive assemblies, arms, forearm assemblies, adaptors, and other applicable parts are described for example in U.S. Pat. Nos. 6,331,181, 6,491,701, and 6,770,081, the full disclosures of which are incorporated herein by reference for all purposes.

It is noted that various surgical instruments may be improved in accordance with the present invention, including but not limited to tools with and without end effectors, such as jaws, scissors, graspers, needle holders, micro-dissectors, staple appliers, tackers, suction irrigation tools, clip appliers, cutting blades, irrigators, catheters, and suction orifices. Alternatively, the surgical instrument may comprise an electrosurgical probe for ablating, resecting, cutting or coagulating tissue. Such surgical instruments are available from Intuitive Surgical, Inc. of Sunnyvale, Calif.

For the methods and apparatus mentioned above, it may be advantageous to use a calibration process in which combinations of forces and torques are applied to the instrument tip serially or in simultaneous combinations while correction factors and offsets are determined. The correction factors and offsets may then be applied to the theoretical equations for combining the gauge outputs to obtain $F_x$, $F_y$, and reject $F_z$, $T_x$, and $T_y$. Such a calibration process may be done either by directly calculating the correction factors and offsets or by a learning system such as a neural network embedded in the calibration fixture or in the instrument itself. In any calibration method, the calibration data may be programmed into an integrated circuit embedded in the instrument so that the surgical system using the individual instrument can correctly identify and apply its correction factors and offsets while the instrument is in use.

Advantageously, force sensor apparatus 100 is adaptable to the size and shape constraints of various robotic surgical instruments and is suitable for a variety of instruments. Accordingly, end portions 102b, 102c may be formed into various applicable shapes and sizes. Furthermore, force sensor apparatus 100 may be manufactured, tested, and calibrated as a separate modular component and brought together with other components in the conventional instrument assembly process. Also, the sensor may be a slip-on module with suitable electrical contacts that mate with contacts on the instrument shaft permitting a higher value sensor to be used with lower cost instruments of limited cycle life. In addition, the sensor structural member 102 may be comprised of an advantageous material, which may be the same or a different material than the instrument shaft 110 whose design considerations may compromise the properties required for the sensor.

Referring now to FIGS. 4A through 4D, a force sensor apparatus 200 is illustrated. The descriptions of substantially similar parts or elements as those described above with respect to FIGS. 3A-3C are applicable in this embodiment with respect to FIGS. 4A-4D, and redundant descriptions may be omitted.

Figure 4A:
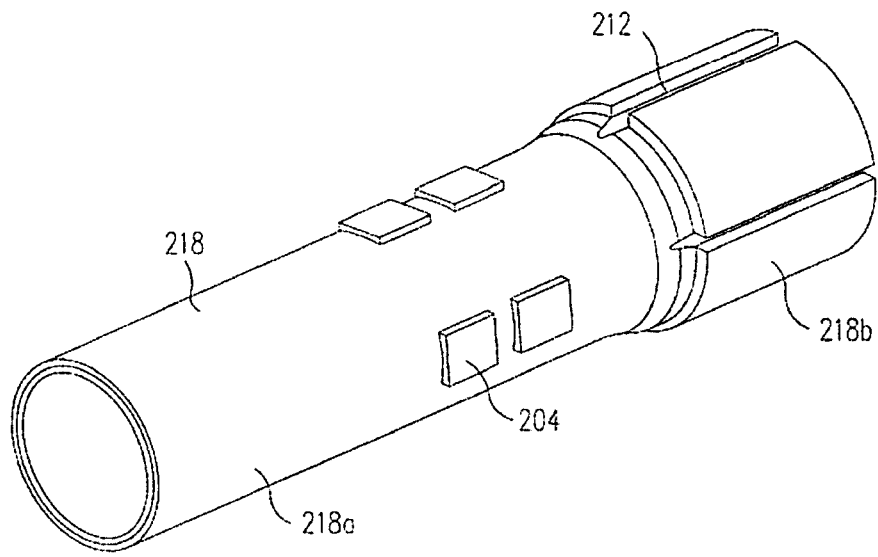
FIG. 4A is a perspective view of an inner tube of another force sensor apparatus.

FIG. 4A is a perspective view of an inner tube 218 of force sensor apparatus 200. Inner tube 218 includes a proximal raised end portion 218b and a depressed portion 218a smaller in diameter than raised end portion 218b. Strain gauges, as described above with respect to FIGS. 3A-3C, may be mounted on the surface of depressed portion 218a. Raised end portion 218b may include grooves 212 for routing of wire leads or optic fibers from strain gauges 204.

Figure 4B:
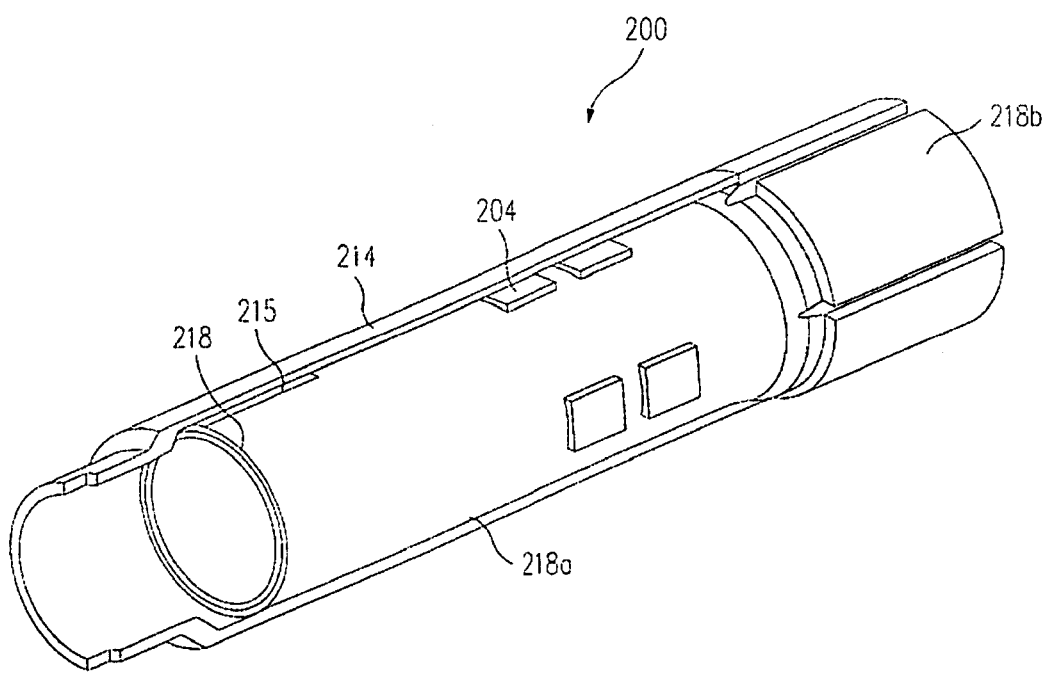
FIG. 4B is a partial cross-sectional view of an outer tube/cover over the inner tube of FIG. 4A of the force sensor apparatus.
Figure 4C:
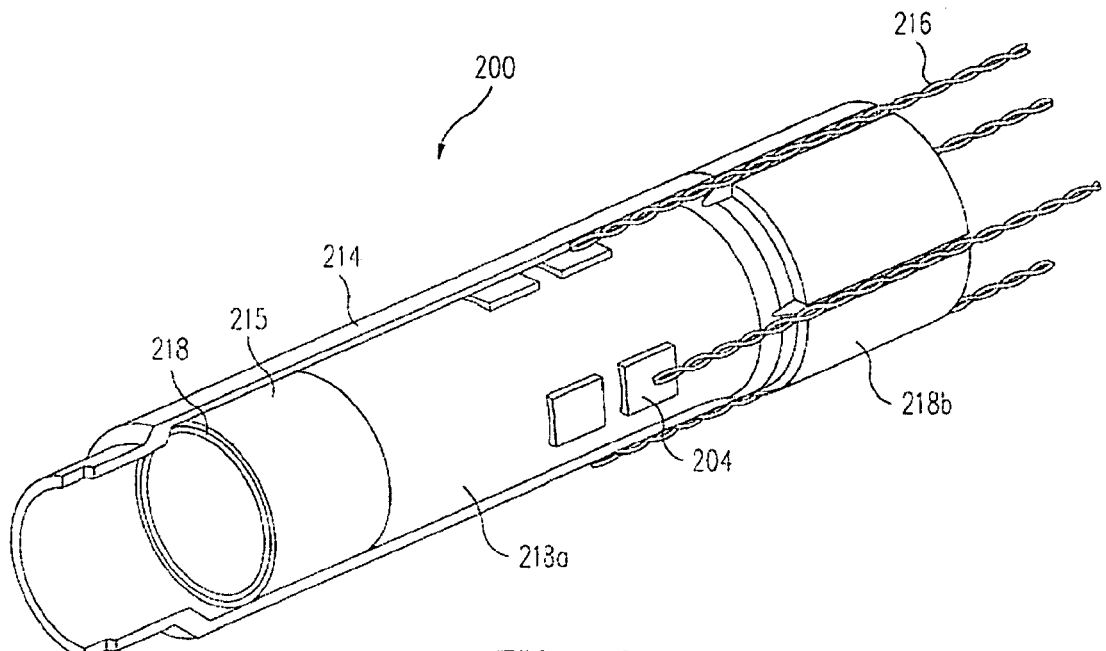
FIG. 4C shows intervening material between the inner and outer tubes of FIG. 4B of the force sensor apparatus and wires or optic fibers operably coupled to the force sensor apparatus.
Figure 4D:
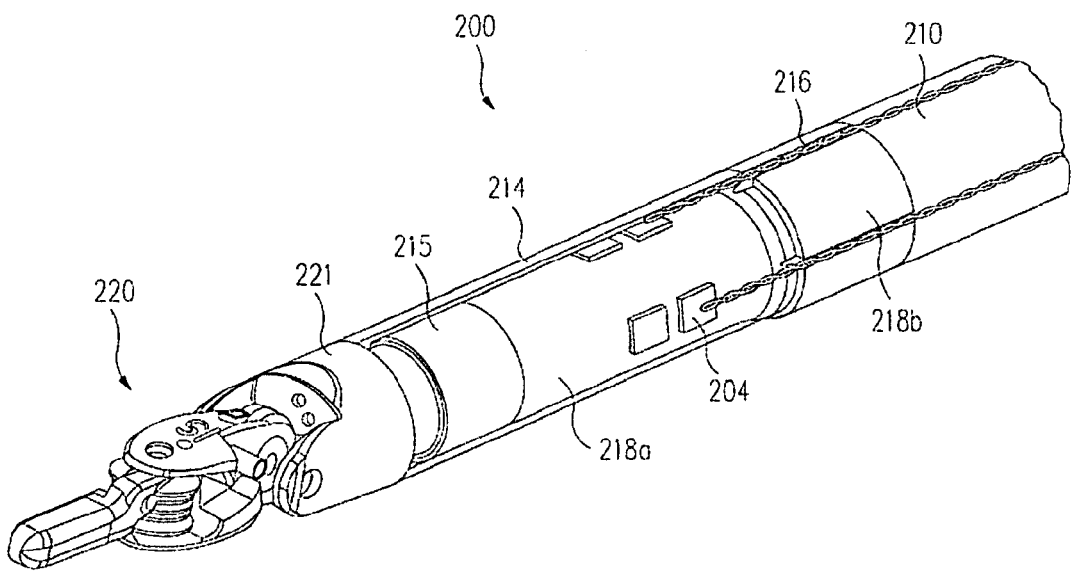
FIG. 4D shows a partial cross-sectional view of the force sensor apparatus operably coupled proximal to (or inboard of) a wrist joint of a surgical instrument.

FIG. 4B is a partial cross-sectional view of an outer tube 214 over the inner tube 218. In one example, outer tube 214 can provide mechanical and thermal protection of strain gauges 204 on inner tube 218. FIG. 4C highlights elastomeric material 215 between inner tube 218 and outer tube 214 maintaining concentricity of the tubes. Leads or optic fibers 216 connecting gauges 204 with data acquisition means are inlaid into grooves 212 and may be potted in place with epoxy or other adhesive. Finally in FIG. 4D wrist 221 and end effector 220 are connected distally to tube 214.

Figure 5A:
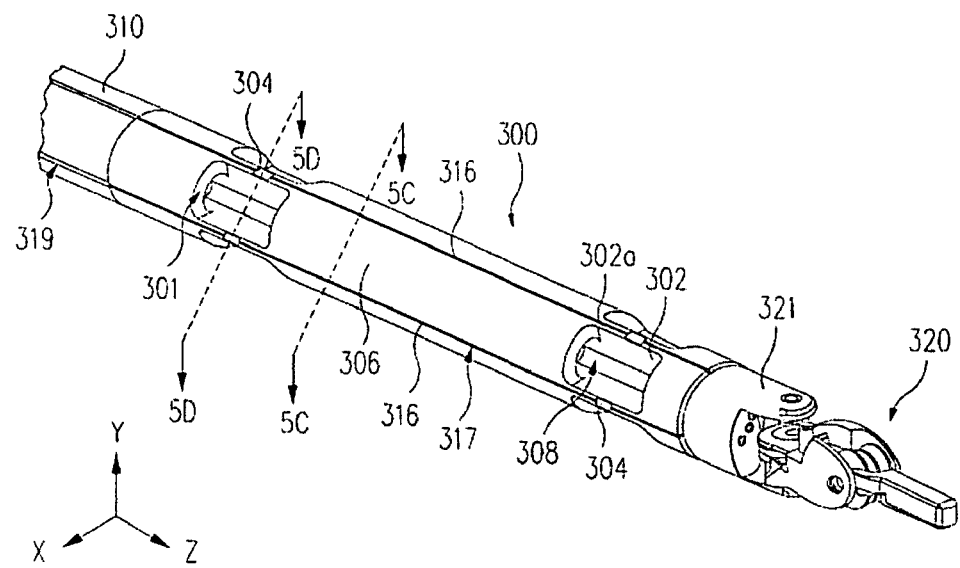
FIG. 5A is a perspective view of a force sensor apparatus in accordance with yet another embodiment of the present invention.
Figure 5B:
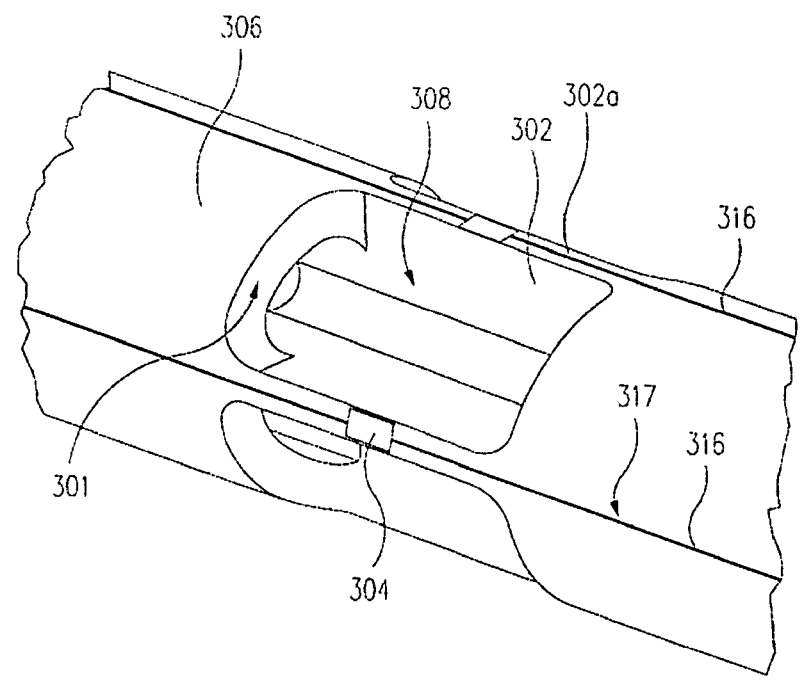
FIG. 5B illustrates an enlarged perspective view of a section of the force sensor apparatus of FIG. 5A.
Figure 5C:
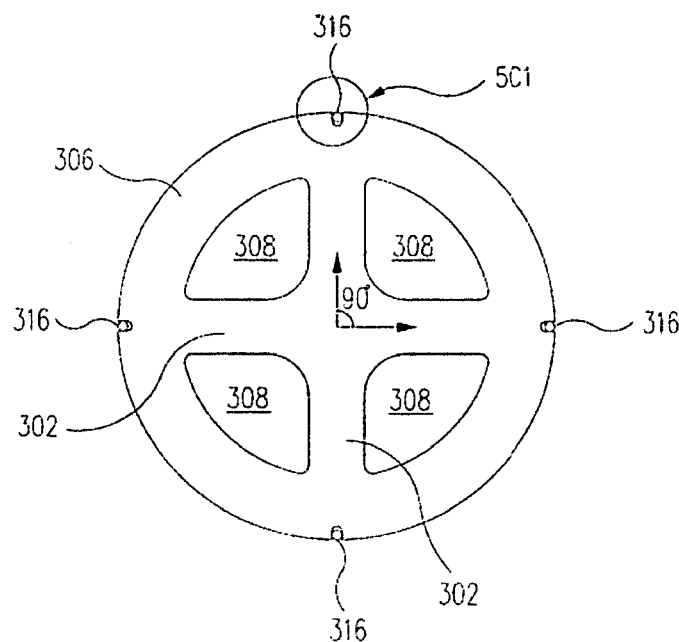
FIG. 5C illustrates a cross-sectional view of the force sensor apparatus of FIG. 5A along line 5C-5C.
Figure 5D:
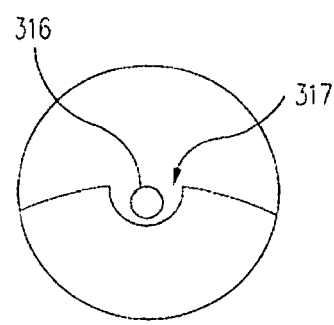
FIG. 5D illustrates a cross-sectional view of the force sensor apparatus of FIG. 5A along line 5D-5D.
Figure 5D:
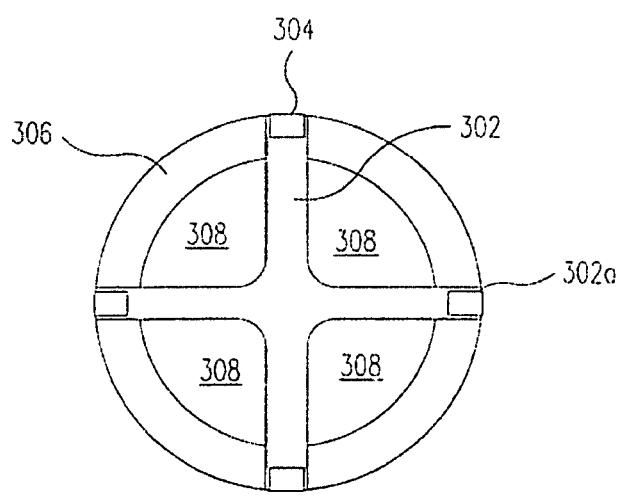
Figure 5E:
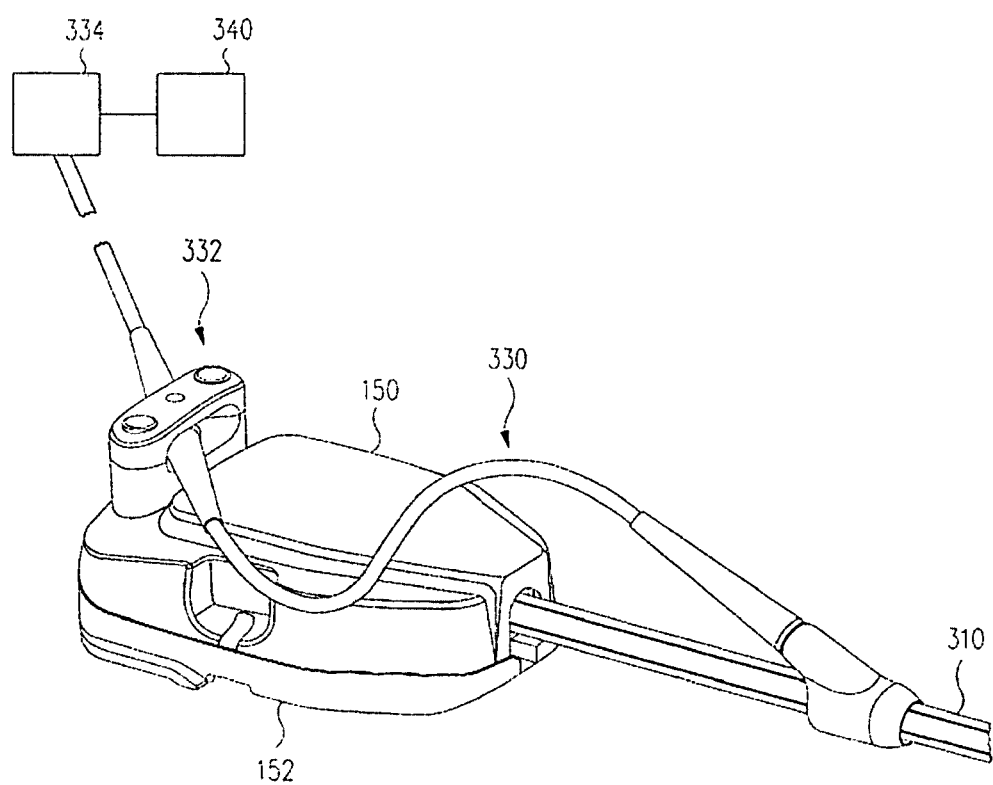
FIG. 5E illustrates a strain relief for strain gauge wires or optic fibers in accordance with an embodiment of the present invention.

Referring now to FIGS. 5A-5E, views of a surgical instrument including another force sensor apparatus 300 is illustrated in accordance with yet another embodiment of the present invention. An end portion 320, such as a surgical end effector, is coupled to force sensor apparatus 300 via a wrist joint 321. A housing 150 (FIG. 5E) is operably coupled to a proximal end of a rigid shaft 310, the housing 150 further including an interface 152 which mechanically and electrically couples the instrument to the manipulator 51 (FIG. 1B). FIG. 5B is an enlarged perspective view of an aperture and rib section of the force sensor apparatus of FIG. 5A. FIGS. 5C and 5D are cross-sectional views of the force sensor apparatus of FIG. 5A along lines 5C-5C and 5D-5D, respectively, and FIG. 5C illustrates a magnified section labeled 5C1 in FIG. 5C. FIG. 5E illustrates an example proximal portion of the surgical instrument including the housing and operably coupling of the instrument to an interrogator 334 and processor 340. The descriptions of substantially similar parts or elements as those described above with respect to FIGS. 1-4 are applicable in this embodiment with respect to FIGS. 5A-5E, although redundant descriptions may be omitted.

Returning to FIG. 5A, force sensor apparatus 300 includes a generally annular tube 306 operably coupled to a distal end of rigid shaft 310 and proximal to wrist joint 321 in accordance with an embodiment of the present invention. In one embodiment, tube 306 includes a number of rectangular-shaped apertures 301 cut from tube 306 and a plurality of radial ribs 302 forming through passages 308 for passage of actuation cables, wires, tubes, rods, cautery wires and/or flushing fluids. Ribs 302 run along and radiate from the z-axis centerline of tube 306, and a number (e.g., 3, 4, 6, or 8) of strain gauges 304 are oriented parallel to the lengthwise z-axis of the tube and mounted to an outer rib surface 302a. The strain gauges may be inlaid into grooves or a depressed area 317 on the outer rib surface 302a in one example.

In the embodiment illustrated in FIGS. 5A-5D, force sensor apparatus 300 includes two sets of four apertures 301 cut from the wall of tube 306 at separate axial locations along tube 306. Each of the ribs 302 are separated by 90 degrees measured about the z-axis centerline of tube 306, which forms a cruciform cross-sectional view of the ribs 302, as shown in FIGS. 5C and 5D. Ribs 302 form four through passages 308. Furthermore, ribs 302 may extend along the entire length of tube 306 thereby forming internal through passages 308 along the entire length of tube 306, or ribs 302 may extend along a portion(s) of the length of tube 306, thereby forming internal through passages along a portion or portions of the length of tube 306.

Force sensor apparatus 300 is capable of sensing bending moments due to lateral forces applied to the wrist joint 321 or its specialized end portion 320. Advantageously, apertures 301 and ribs 302 provide for regions of controlled stress and strain when subjected to bending moments, which may be measured by fiber optic strain gauges 304 embedded in grooves 317 along an outer surface of the ribs and sensor body parallel to the lengthwise z-axis of tube 306. Through passages 308 permit cables, wires, tubes, or rigid tendons to pass through the sensor apparatus body to actuate the distal wrist joint(s) and/or control the end portion.

In one example, tube 306 and ribs 302 may be made of a sufficiently strong but elastic material to allow sensing of stress and strain without mechanical failure. Tube 306 and ribs 302 are further comprised of material with a sufficiently low modulus of elasticity to give a sufficient strain signal under an applied load, a sufficiently high strain at yield to give adequate safety margin above the maximum design load, and a sufficiently high thermal diffusivity to promote rapid thermal equilibrium (therefore reducing thermal disturbances to sensor output signals) when subject to localized or asymmetric thermal disturbances from tissue contact or endoscope illumination. In particular, the plurality of radial ribs 302 may be comprised of a high thermal diffusivity material, such as an aluminum alloy (e.g., 6061-T6 aluminum) or a copper alloy (e.g., GlidCop® AL-60) or a silver alloy to reduce the temperature difference between opposing gauges under transient thermal disturbances by providing a direct thermal pathway between opposing gauges.

In one example, tube 306 may be comprised of metal alloys, treated metals, or plated metals, such as of aluminum, copper, or silver, which allow for adequate strain, mechanical failure safety margin, and high thermal diffusivity. In a further example, 6061-T6 aluminum, which is an aluminum alloy that is heat treated and aged, GlidCop® AL-60, which is copper that is dispersion strengthened with ultrafine particles of aluminum oxide, or a dispersion strengthened silver, may be used to form tube 306 and ribs 302. Accordingly, both the plurality of ribs and the tube 302 may be comprised of a high thermal diffusivity material, such as an aluminum alloy (e.g., 6061-T6 aluminum) or a copper alloy (e.g., GlidCop® AL-60) or silver alloy to reduce transient and/or steady-state temperature differences between groups of strain gauges separated along the z-axis.

Advantageously, the present invention allows for a low bending moment of inertia to increase a strain signal to noise signal ratio consistent with a materials choice and rib design meeting the need for high thermal diffusivity and a direct thermal path between opposing strain gauges while also providing passage for actuation cables, wires, tubes, and/or rods.

Wire leads or optic fibers 316 (e.g., shielded twisted pairs, coax, or fiber) coupled to the strain gauges 304 may be inlaid into grooves 317 on tube 306, the outer rib surface 302a, and matching grooves 319 in shaft 310 of the surgical instrument. The wire leads or optic fibers 316 may then be embedded in an adhesive potting compound such as epoxy.

As disclosed in U.S. patent application Ser. No. 11/537, 241, filed Sep. 29, 2006, the contents of which have been previously incorporated by reference, strain gauges 304 may be spaced in a ring at intervals around the circumference of the tube 306 mounted on ribs 302 (e.g., 3 gauges at 120 degrees, 4 gauges at 90 degrees, 4 gauges at 70 and 110 degrees or other supplementary pairs of angles). The signals from the sensors are combined arithmetically in various sums and differences to obtain measures of the transverse forces $F_x$, $F_y$, and to reject axial forces $F_z$ exerted upon the instrument tip and to reject wrist torques about the two axes perpendicular to the shaft axis (i.e., axes x and y). In accordance with the present invention, the measurement of the transverse forces is made independent of the orientation and effective lever arm length of an articulated wrist mechanism at the distal end of the instrument as well as wrist friction moments and actuator cable tensions when two axially separated sets or rings of gauges are utilized. Forces exerted against end portion 320 are detected by the force sensing elements, which may be operably coupled to the servo control or surgeon display means via an interrogator 334 and to a processor 340 for notifying the surgeon of these forces (e.g., via master(s) or a display means). It is understood that by adding a second ring of similarly oriented gauges (e.g., two sets of 3 gauges or two sets of 4 gauges) at a different position along the z-axis of the tube, additional side load-induced moment information can be obtained, and dependence of the force data on instrument wrist length, orientation, and resulting jaw distance and cable tensions, can be eliminated.

In one example, various strain gauges may be used, including but not limited to conventional foil type resistance gauges, semiconductor gauges, optic fiber type gauges using Bragg grating or Fabry-Perot technology, or others, such as strain sensing surface acoustic wave (SAW) devices. Optic fiber Bragg grating (FBG) gauges may be advantageous in that two sensing elements may be located along one fiber at a known separation, thereby only requiring the provision of four fibers along the instrument shaft. Fiber optic gauges may also be desirable because of their immunity to disturbance from cautery and other electromagnetic noise.

A problem with the use of FBG strain gauges in conventional fiber such as SMF-28 is their inherent positive temperature sensitivity, being especially problematic when the FBG strain gauges are mounted to materials with a positive thermal expansion coefficient, which adds to the temperature sensitivity of the FGB strain gauges. Temperature sensitivity limits the accuracy of a force transducer utilizing FBGs and positive thermal expansion coefficient substrate materials, especially under asymmetric transient thermal loads that may occur in surgery.

Intrinsic and extrinsic temperature compensation of FBG strain sensors may be accomplished with additional gratings written in the same or nearby region of the fiber and may include the use of additional fibers, exotic doped fibers spliced together, highly bi-refringent fiber or other means to differentiate thermal responses so that simultaneous equations in strain and temperature with respect to wavelength shift can be solved to obtain the strain independent of the temperature of any single grating. These methods typically require additional interrogator channels or exotic interrogation methods.

In another example, the plurality of fiber optic strain gauges 304 may be comprised of a negative thermo-optic coefficient optical fiber material, such as binary or ternary phosphate glass fiber, fluoride glass fiber, oxy-fluoride glass fiber, tellurite glass fiber, or a polymer fiber. The negative thermo-optic coefficient fiber advantageously reduces or eliminates the combined effect of a positive thermo-optic coefficient fiber, such as SMF-28 or other doped fiber, and the positive thermal expansion coefficient of the sensor body material.

Advantageously, embodiments of the present invention provide apparatus and methods for improved thermal stability when subjected to temperature changes, such as when entering the patient body from a lower temperature operating room environment, contacting warm living tissue, absorbing incident light from an endoscope illuminator, or other source of thermal disturbance that may occur during surgery. Also, the present invention provides for cost savings, relative ease of manufacture, higher field reliability, and accurate strain measurements.

Both FBG and Fabry-Perot fiber technologies require an interrogator unit, such as interrogator unit 334 (FIG. 5E) that decodes the optically encoded strain information into electrical signals compatible with the computer control hardware of the robotic surgical system. A processor 340 (FIG. 5E) operably coupled to the interrogator unit 334 may then be used to calculate forces according to the signals from the strain gauges/sensors.

For resistive foil or semiconductor strain gauges, active components such as bare die op-amps and passive components such as secondary resistors or capacitors may be attached adjacent to the strain gauges connected by bond wires or thick film circuit traces in the manner of hybrid circuits to amplify, filter, and/or modulate the gauge output signals to reject noise sources. Such components are not needed for fiber optic gauges.

In accordance with an embodiment of the present invention, force sensor apparatus 300 is a separately manufactured module or part adapted for incorporation as part of the shaft 310 of a laparoscopic surgical instrument at a prescribed distance from the tip where there may be an articulated wrist with specialized jaws, cutting devices, or other end portion 320. A proximal portion of tube 306 operably couples to the shaft 310 of the surgical instrument and a distal portion of tube 306 operably couples to wrist joint 321. In one example, the diameter of the completed force sensor apparatus matches the diameter of the instrument shaft, thus allowing the entire assembly of the instrument (including the coupled force sensor apparatus) to pass through a cannula or a seal without added friction or snagging. In other embodiments, the surgical instrument may be manufactured with a force sensor portion integrated as a part of shaft 310 (i.e., force sensor apparatus 300 is not separable from the shaft).

Similar to the embodiments described above, the surgical instrument to which force sensor apparatus 300 couples may also include a service loop 330 (FIG. 5E) of conductive traces or optic fibers at the proximal end of the instrument shaft 310 and a cable swivel mechanism 332 permitting the substantially free rotation of the instrument shaft while conducting the input gauge excitation power or light and electrical or optical output gauge signals to the interrogator unit 334.

Similar to the embodiments described above, the housing 150 operably interfaces with a robotic manipulator arm, in one embodiment via a sterile adaptor interface. Applicable housings, sterile adaptor interfaces, and manipulator arms are disclosed in U.S. patent application Ser. No. 11/314,040 filed on Dec. 20, 2005, and U.S. patent application Ser. No. 11/613,800 filed on Dec. 20, 2006, the full disclosures of which are incorporated by reference herein for all purposes. Examples of applicable shafts, end portions, housings, sterile adaptors, and manipulator arms are manufactured by Intuitive Surgical, Inc. of Sunnyvale, Calif.

In a preferred configuration, end portion 320 has a range of motion that includes pitch and yaw motion about the x- and y-axes and rotation about the z-axis. These motions as well as actuation of an end effector are provided via cables in the housing 150 and cables and/or rods running through the shaft and into the housing that transfer motion from the manipulator arm. Embodiments of drive assemblies, arms, forearm assemblies, adaptors, and other applicable parts are described for example in U.S. Pat. Nos. 6,331,181, 6,491,701, and 6,770,081, the full disclosures of which are incorporated herein by reference for all purposes.

It is noted that various surgical instruments may be improved in accordance with the present invention, including but not limited to tools with and without end effectors, such as jaws, scissors, graspers, needle holders, micro-dissectors, staple appliers, tackers, suction irrigation tools, clip appliers, cutting blades, hooks, sealers, lasers, irrigators, catheters, and suction orifices. Alternatively, the surgical instrument may comprise an electrosurgical probe for ablating, resecting, cutting or coagulating tissue. Such surgical instruments are manufactured by Intuitive Surgical, Inc. of Sunnyvale, Calif.

For the sensing methods and apparatus mentioned above, it may be advantageous to use a calibration process in which combinations of forces and torques are applied to the instrument tip serially, simultaneously, or in combinations while correction factors and offsets are determined to apply to the theoretical equations for combining the gauge outputs to obtain $F_x$, $F_y$ and reject $F_z$, $T_x$, and $T_y$. This calibration may be done either by directly calculating the correction factors and offsets or by a learning system such as a neural network embedded in the calibration fixture or in the instrument itself. In any calibration method, the calibration data may be programmed into an integrated circuit embedded in the instrument so that the surgical system using the individual instrument can correctly identify and apply its correction factors and offsets while the instrument is in use.

Advantageously, force sensor apparatus 300 of the present invention is adaptable to the size and shape constraints of robotic endoscopic surgical instruments and is suitable for a variety of instruments. Furthermore, force sensor apparatus 300 may be manufactured, tested, and calibrated as a separate modular component and brought together with other components in the conventional instrument assembly process or as an integrated part of the instrument shaft 310. Also, the sensor may be a slip-on module permitting a higher value sensor to be used with lower cost instruments of limited cycle life.

The present invention is not limited to rib orientation or a certain number of ribs, sets of ribs, strain gauges, or tube apertures, and FIGS. 6A-6C1, 7A-7B1, 8, and 9A-9C illustrate force sensor apparatus in accordance with other embodiments of the present invention. The descriptions of substantially similar parts or elements as those described above with respect to FIGS. 5A-5E are applicable in these embodiments although redundant descriptions may be omitted.

Figure 6A:
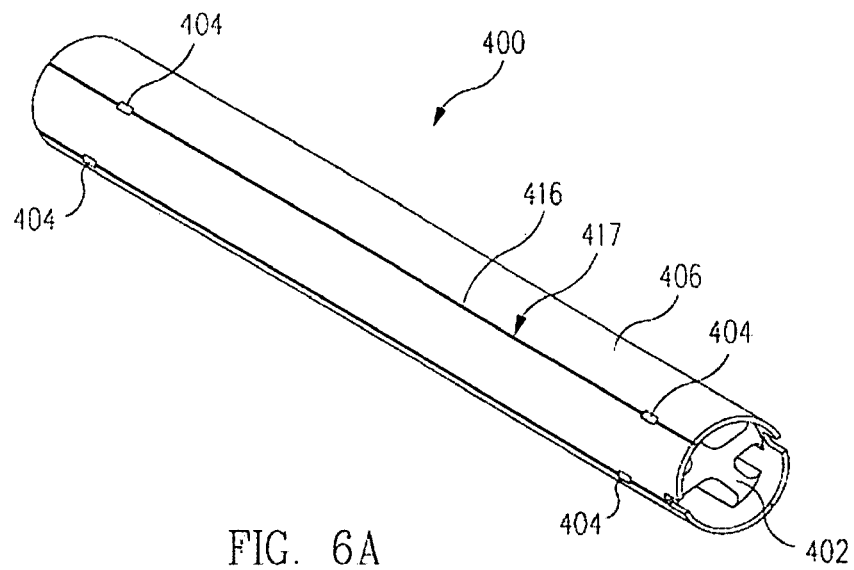
FIGS. 6A and 6B illustrate perspective views of another force sensor apparatus and an enlarged view of a portion of the force sensor apparatus in accordance with another embodiment of the present invention.
Figure 6B:
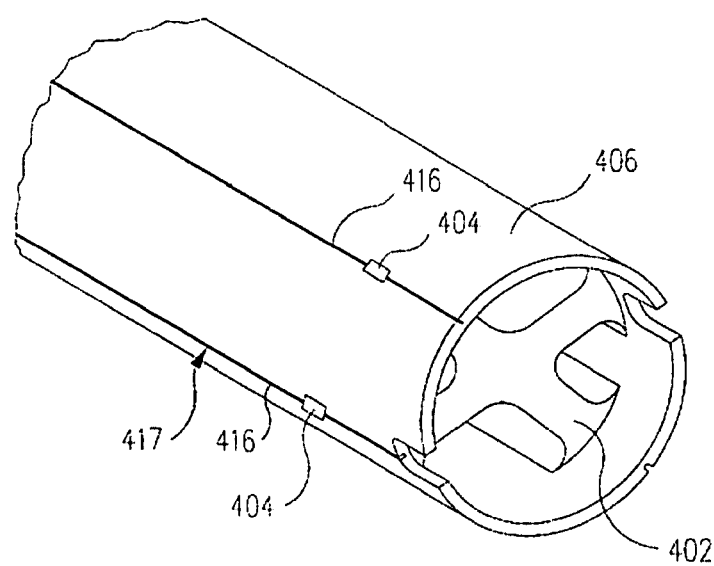

Referring now to FIGS. 6A-6C1, a force sensor apparatus 400 is illustrated, the force sensor apparatus 400 including four ribs 402 in diametrically opposite pairs at skewed supplementary angles (e.g., 70 degrees and 110 degrees) about a z-axis centerline of a tube 406. Ribs 402 extend radially within tube 406 from the z-axis centerline of the tube providing four through passages 408a and 408b for passage of actuation cables, wires, tubes, rods, cautery wires and/or flushing fluids. Advantageously, a larger through passage 408a utilizing skewed angles allows for easier passage of cables, wires, tubes, and/or rods through tube 406 (e.g., three hypodermic tubes may be passed per 110 degree channel). In this embodiment, as can be seen in FIG. 6A, tube 406 does not include apertures through the wall of tube 406. However, the combined stiffness of tube 406 and ribs 402 still allow for a strong strain signal to noise signal ratio consistent with a materials choice and rib design meeting the need for high thermal diffusivity and a direct thermal path between opposing strain gauges while also providing passage for actuation cables, wires, tubes, and/or rods.

Similar to the embodiments disclosed above, a number of strain gauges 404 are oriented parallel to the lengthwise z-axis of the tube and mounted to an outer rib surface 402a. The strain gauges may be inlaid into grooves or a depressed area 417 on the outer rib surface 402a in one example. Wire leads or optic fibers 416 (e.g., shielded twisted pairs, coax, or fiber) coupled to the strain gauges 404 may be inlaid into grooves 417 on the outer rib surface 402a of tube 406. The wire leads or optic fibers 416 may then be embedded in an adhesive potting compound such as epoxy.

Referring now in particular to FIGS. 6C and 6C1, an end view of force sensor apparatus 400 and a magnified section labeled 6C1 in FIG. 6C are respectively illustrated. A thermal shielding over the strain gauges may be provided in accordance with another embodiment of the present invention. In one example, a thermal shunt shell 452 is provided over tube 406 with an insulating fluid (gas or liquid) filled or evacuated gap 450 being provided between the outer surface of tube 406 and the inner surface of thermal shunt shell 452. Thermal shunt shell 452 may be comprised of a high thermal diffusivity material, such as an aluminum alloy (e.g., 6061-T6 aluminum) or a copper alloy (e.g., GlidCop® AL-60) or a silver alloy. Optionally, a light reflective surface or coating 453 may be provided over thermal shunt shell 452, which may deflect light and reduce localized heating of the force sensor apparatus, for example from endoscope illumination. An insulating coating 454 may also be provided over thermal shunt shell 452, the insulating coating 454 being comprised of a substantially transparent plastic shrink polymer in one example. Advantageously, the thermal shielding over the sensor tube 406 and the strain gauges 404 as described above allows for more uniform heat/thermal diffusion among the gauges, being particularly advantageous for mitigating asymmetric thermal loads upon the instrument. The thermal shielding described above is applicable for various embodiments of the present invention.

Figure 7A:
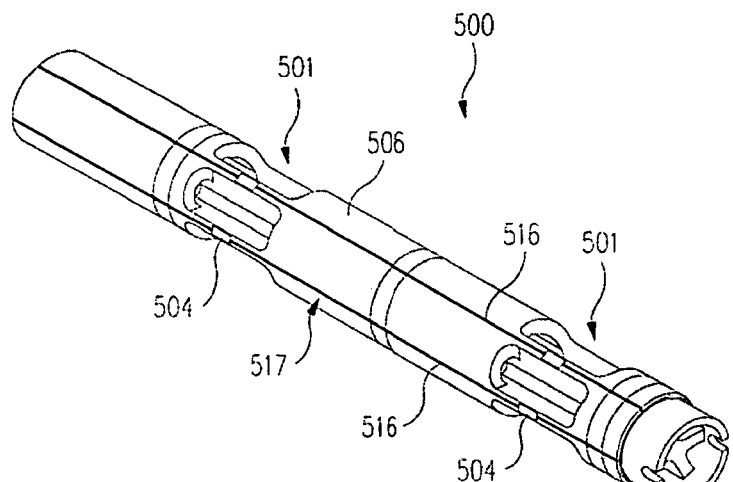
FIGS. 7A and 7B illustrate a perspective view and an end view of another force sensor apparatus including radial ribs positioned in non-uniform supplementary angles and exposed by apertures on the tube surface.
Figure 7B:
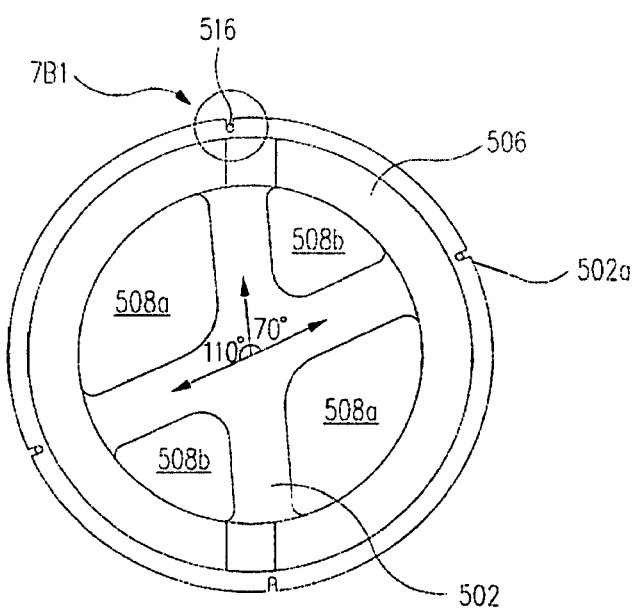

Referring now to FIGS. 7A thru 7B1, a force sensor apparatus 500 is illustrated, the force sensor apparatus 500 including four ribs 502 paired at skewed angles (e.g., 70 degrees and 110 degrees) about a z-axis centerline of a tube 506. Ribs 502 extend radially within tube 506 from the z-axis centerline of the tube providing four through passages 508a and 508b for passage of actuation cables, wires, tubes, rods cautery wires and/or flushing fluids. Advantageously, a larger through passage 508a utilizing skewed angles allows for easier passage of cables, wires, tubes, and/or rods through tube 506 (e.g., three hypodermic tubes may be passed per 110 degree channel). In this embodiment, as can be seen in FIG. 7A, tube 506 include apertures 501 provided through the wall of tube 506. The reduced stiffness of exposed ribs 502 allow for a strong strain signal to noise signal ratio consistent with a materials choice and rib design meeting the need for high thermal diffusivity and a direct thermal path between opposing strain gauges while also providing passage for actuation cables, wires, tubes, rods, and the like.

Similar to the embodiments disclosed above, a number of strain gauges 504 are oriented parallel to the lengthwise z-axis of the tube and mounted to an outer rib surface 502a. The strain gauges may be inlaid into grooves or a depressed area 517 on the outer rib surface 502a in one example. Wire leads or optic fibers 516 (e.g., shielded twisted pairs, coax, or fiber) coupled to the strain gauges 504 may be inlaid into grooves 517 on tube 506, the outer rib surface 502a, and matching grooves 517 in a shaft of the surgical instrument. The wire leads or optic fibers 516 in grooves 517 may then be embedded in an adhesive potting compound such as epoxy.

Figure 8:
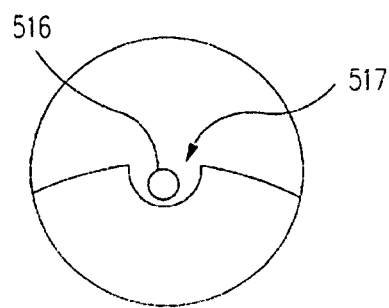
FIG. 8 illustrates an end view of another force sensor apparatus including three radial ribs in accordance with another embodiment of the present invention.
Figure 8:
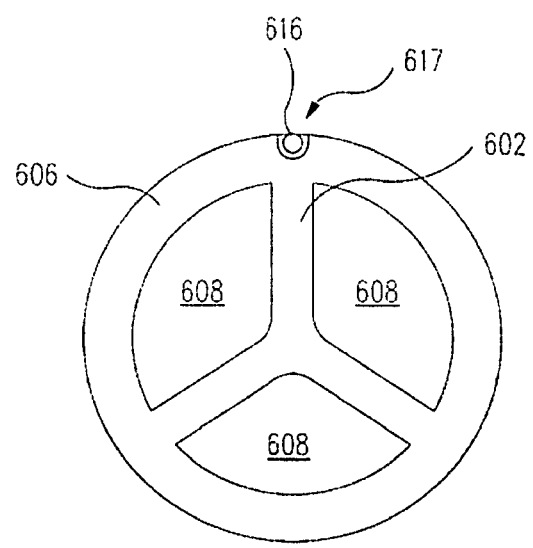

FIG. 8 illustrates a cross-sectional view of another force sensor apparatus which includes three ribs 602 separated by 120 degrees about a z-axis centerline of the force sensor apparatus tube 606. Ribs 602 provide three through passages 608. Wire leads or optic fibers 616 (e.g., shielded twisted pairs, coax, or fiber) coupled to strain gauges may be inlaid into grooves 617 on an instrument tube, an outer rib surface, and matching grooves in a shaft of the surgical instrument.

Figure 9A:
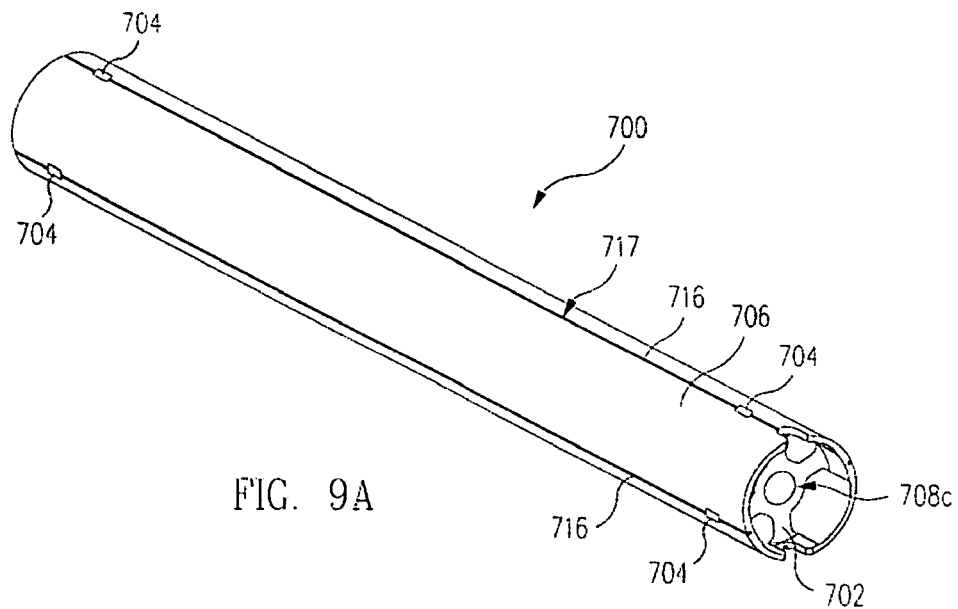
FIGS. 9A and 9B illustrate perspective views of another force sensor apparatus and an enlarged section of the force sensor apparatus, respectively, in accordance with another embodiment of the present invention.
Figure 9B:
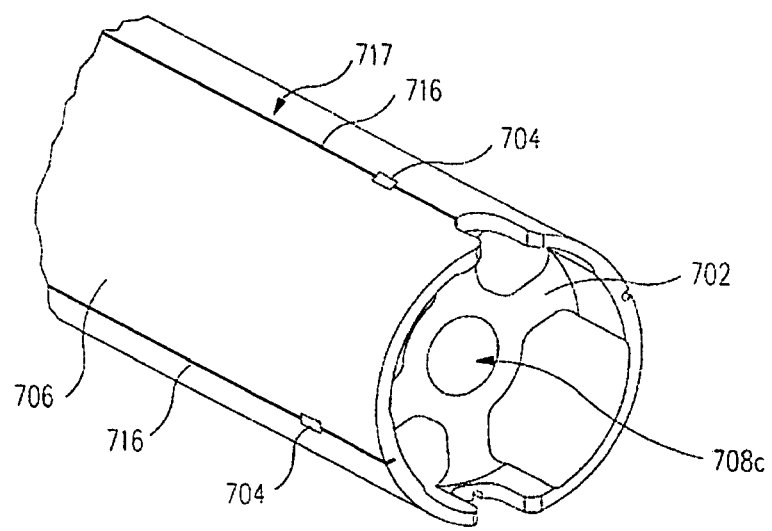
Figure 9C:
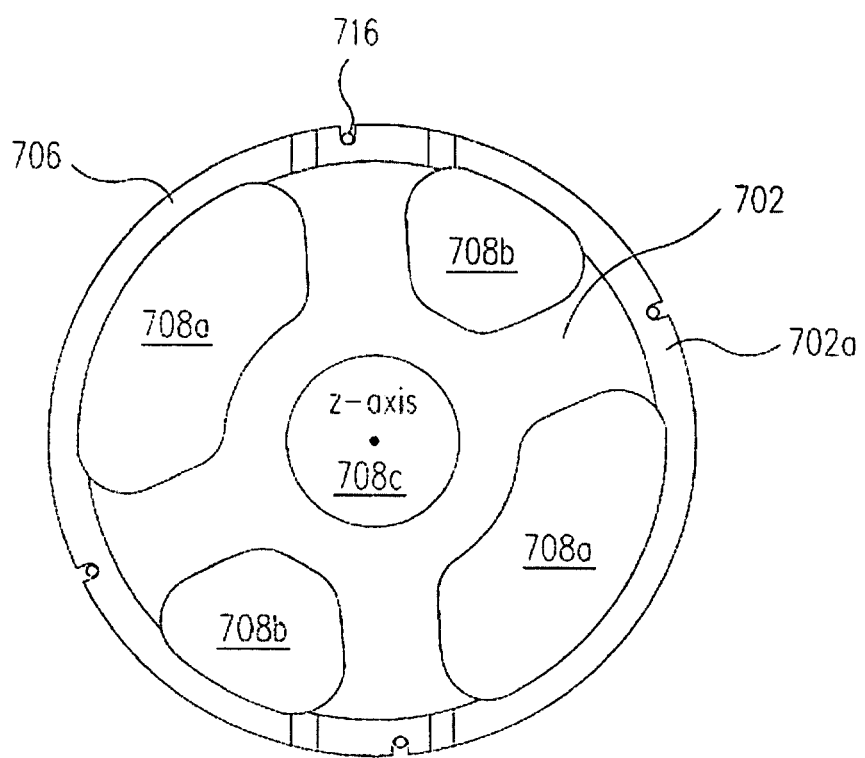
FIG. 9C illustrates an end view of the force sensor apparatus of FIGS. 9A and 9B including radial ribs positioned in non-uniform supplementary angles and a central through passage in accordance with another embodiment of the present invention.

Referring now to FIGS. 9A-9C, a force sensor apparatus 700 is illustrated, the force sensor apparatus 700 including four ribs 702 paired at skewed angles (e.g., 70 degrees and 110 degrees) about a z-axis centerline of a tube 706. Ribs 702 extend radially within tube 706 from the z-axis centerline of the tube providing through passages 708a and 708b. In this embodiment, force sensor apparatus 700 also includes a central through passage 708c along a lengthwise axis of tube 706 in accordance with another embodiment of the present invention. The through passages may be used for passage of actuation cables, wires, tubes, rods, and/or fluids. In this embodiment, as can be seen in FIG. 9A, tube 706 does not include apertures through the wall of the tube but apertures exposing portions of the interior ribs are within the scope of the present invention. Furthermore, the combined stiffness of tube 706 and ribs 702 still allow for a strong strain signal to noise signal ratio consistent with a materials choice and rib design meeting the need for high thermal diffusivity and a thermal path between opposing strain gauges while also providing passage for actuation cables, wires, tubes, rods, and/or fluids.

Similar to the embodiments disclosed above, a number of strain gauges 704 are oriented parallel to the lengthwise z-axis of the tube and mounted to an outer rib surface 702a. The strain gauges may be inlaid into grooves or a depressed area 717 on the outer rib surface 702a in one example. Wire leads or optic fibers 716 (e.g., shielded twisted pairs, coax, or fiber) coupled to the strain gauges 704 may be inlaid into grooves 717 on the outer rib surface 702a of tube 706. The wire leads or optic fibers 716 may then be embedded in an adhesive potting compound such as epoxy.

Figure 10:
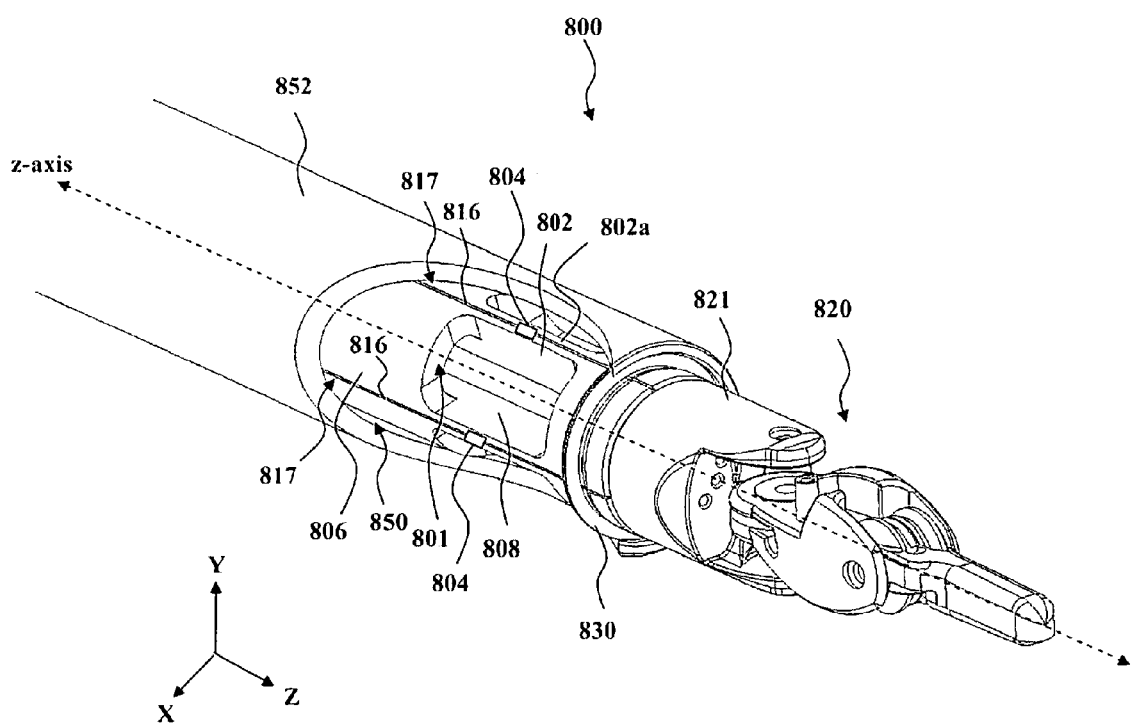
FIG. 10 illustrates a perspective cutaway view of another force sensor apparatus, including apertures exposing radial ribs and a concentric shell surrounding the sensor tube with an annular gap in accordance with an embodiment of the present invention.

Referring now to FIG. 10, a perspective cutaway view of another force sensor apparatus is illustrated in accordance with an embodiment of the present invention. The descriptions of substantially similar parts or elements as those described above with respect to FIGS. 1A-9C are applicable in this embodiment with respect to FIG. 10, although redundant descriptions may be omitted. Force sensor apparatus 800 includes a generally annular tube 806 operably coupled to an end portion 820 via a wrist joint 821. In this embodiment, tube 806 includes a number of rectangular-shaped apertures 801 cut from tube 806 and a plurality of radial ribs 802 forming through passages 808 for passage of wrist actuation cables, wires, tubes, or rods, cautery wires and/or flushing fluids. Ribs 802 run along and radiate from the z-axis centerline of tube 806, and a plurality of strain gauges 804 are oriented parallel to the lengthwise z-axis of the tube and mounted to an outer rib surface 802a. The strain gauges may be inlaid into grooves or a depressed area 817 on the outer rib surface 802a in one example. Wire leads or optic fibers 816 (e.g., shielded twisted pairs, coax, or fiber) coupled to the strain gauges 804 may be inlaid into grooves 817 on the outer rib surface 802a of tube 806. The wire leads or optic fibers 816 may then be embedded in an adhesive potting compound such as epoxy.

In this embodiment, each of the ribs 802 are separated by 90 degrees measured about the z-axis centerline of tube 806, which forms a cruciform cross-sectional view of the ribs 802. Other separation angles for the ribs are within the scope of the present invention, as outlined above. Furthermore, ribs 802 may extend along the entire length of tube 806 thereby forming internal through passages 808 along the entire length of tube 806, or ribs 802 may extend along a portion(s) of the length of tube 806, thereby forming internal through passages along a portion or portions of the length of tube 806.

Similar to the embodiments described above, force sensor apparatus 800 is capable of sensing bending moments due to lateral forces applied to the wrist joint 821 or its specialized end portion 820. Advantageously, apertures 801 and ribs 802 provide for regions of controlled stress and strain when subjected to bending moments, which may be measured by the fiber optic strain gauges 804 embedded in the grooves 817 along the outer surface of the ribs and sensor body parallel to the lengthwise z-axis of tube 806.

In one example, tube 806 and ribs 802 may be comprised of material with a sufficiently low modulus of elasticity to give a sufficient strain signal under an applied load, a sufficiently high strain at yield to give adequate safety margin above the maximum design load, and a sufficiently high thermal diffusivity to promote rapid thermal equilibrium (therefore reducing thermal disturbances to sensor output signals) when subject to localized or asymmetric thermal disturbances from tissue contact or endoscope illumination. In particular, the plurality of radial ribs 802 may be comprised of a high thermal diffusivity material, such as an aluminum alloy (e.g., 6061-T6 aluminum) or a copper alloy (e.g., GlidCop® AL-60) or silver alloy to reduce the temperature difference between opposing gauges under transient thermal disturbances by providing a direct thermal pathway between opposing gauges. In yet another example, the plurality of fiber optic gauges 804 may be comprised of a negative thermo-optic coefficient optical fiber material, such as binary or ternary phosphate glass fiber, fluoride glass fiber, oxy-fluoride glass fiber, tellurite glass fiber, or a polymer fiber. The negative thermo-optic coefficient fiber advantageously reduces or eliminates the combined effect of a positive thermo-optic coefficient fiber, such as SMF-28 or other doped fiber, and the positive thermal expansion coefficient of the sensor body material.

In one example, tube 806 may be comprised of metal alloys, treated metals, or plated metals, such as of aluminum, copper, or silver, which allow for adequate strain, mechanical failure safety margin, and high thermal diffusivity. In a further example, 6061-T6 aluminum, which is an aluminum alloy that is heat treated and aged, GlidCop® AL-60, which is copper that is dispersion strengthened with ultrafine particles of aluminum oxide, or a dispersion strengthened silver, may be used to form both tube 806 and ribs 802. Accordingly, both the plurality of ribs 802 and the tube 806 may be comprised of a high thermal diffusivity material, such as an aluminum alloy (e.g., 6061-T6 aluminum) or a copper alloy (e.g., GlidCop® AL-60) or silver alloy, to reduce transient and/or steady-state temperature differences between groups of strain gauges separated along the z-axis.

Similar to the embodiment described above with respect to FIGS. 6A-6C1, a thermal shielding may be provided over the strain gauges 804 in accordance with another embodiment of the present invention. In one example, a thermal shunt shell 852 is provided over tube 806 with an insulating fluid (gas or liquid) filled or evacuated gap 850 being provided between the outer surface of tube 806 and the inner surface of thermal shunt shell 852. Thermal shunt shell 852 may be mechanically and thermally isolated from the strain gauges by providing compliant elastomer rings 830 between the shunt shell 852 and the tube 806 to prevent interference with the applied surgical forces and to insulate the sensor. Thermal shunt shell 852 may be comprised of a high diffusivity material, such as an aluminum alloy (e.g., 6061-T6 aluminum) or a copper alloy (e.g., GlidCop® AL-60) or silver alloy. Optionally, a light reflective surface or coating may be provided over thermal shunt shell 852, which may deflect light and reduce localized heating of the force sensor apparatus, for example from endoscope illumination. An insulating coating may also be provided over thermal shunt shell 852, the insulating coating being comprised of a substantially transparent plastic shrink polymer in one example. Advantageously, the thermal shielding over the strain gauges as described above allows for more uniform heat/thermal diffusion among the sensors, being particularly advantageous for mitigating asymmetric or transient thermal loads upon the instrument. The thermal shielding described above is applicable for various embodiments of the present invention.

Figure 11A:
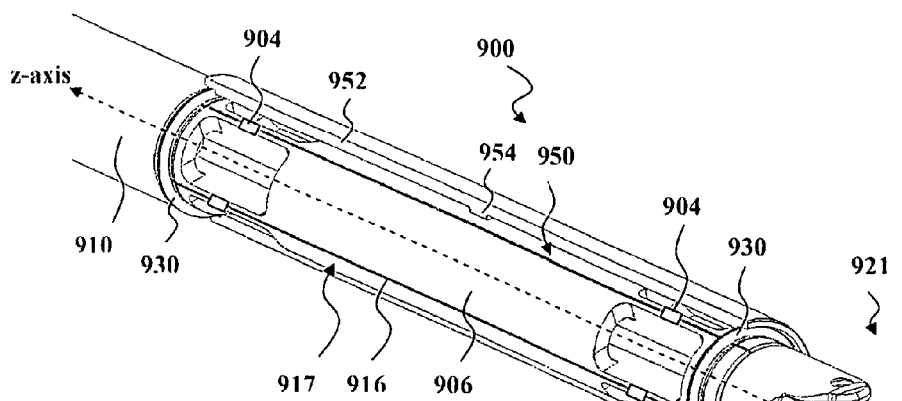
FIGS. 11A-11C illustrate different views of another force sensor apparatus, including a concentric shell surrounding the sensor tube with an annular heat conducting rib in accordance with an embodiment of the present invention.
Figure 11B:
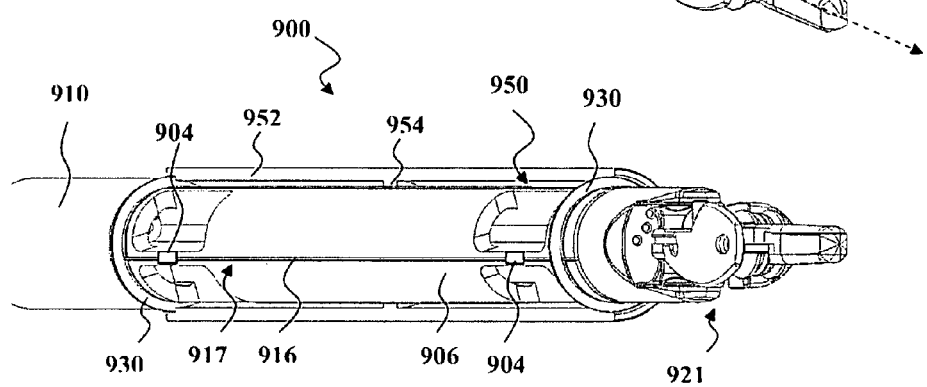
Figure 11C:
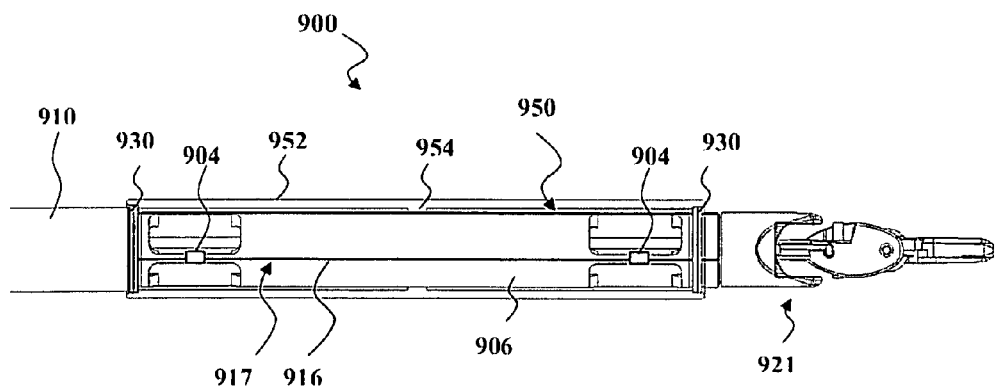

Referring now to FIGS. 11A-11C, different views of another force sensor apparatus is illustrated in accordance with an embodiment of the present invention. The descriptions of substantially similar parts or elements as those described above with respect to FIGS. 1A-10 are applicable in this embodiment with respect to FIGS. 11A-11C, although redundant descriptions may be omitted. A force sensor apparatus 900 includes a generally annular tube 906 operably coupled to an end effector via a wrist joint 921. In this embodiment, tube 906 includes a plurality of radial ribs forming through passages for passage of wrist actuation cables, wires, tubes, or rods, cautery wires, flushing fluids, and the like. A plurality of strain gauges 904 are oriented parallel to the lengthwise z-axis of the tube and mounted to an outer rib surface. The strain gauges may be inlaid into grooves or a depressed area 917 on the outer rib surface in one example. Wire leads or optic fibers 916 (e.g., shielded twisted pairs, coax, or fiber) coupled to the strain gauges 904 may be inlaid into grooves 917 on the outer rib surface of tube 906. The wire leads or optic fibers 916 may then be embedded in an adhesive potting compound such as epoxy.

In this embodiment, each of the ribs may be separated by 90 degrees measured about the z-axis centerline of tube 906, which forms a cruciform cross-sectional view of the ribs. Other separation angles for the ribs are within the scope of the present invention, as outlined above. Furthermore, the ribs may extend along the entire length of tube 906 thereby forming internal through passages along the entire length of tube 906, or the ribs may extend along a portion(s) of the length of tube 906, thereby forming internal through passages along a portion or portions of the length of tube 906.

Similar to the embodiments described above, force sensor apparatus 900 is capable of sensing bending moments due to lateral forces applied to the wrist joint or its specialized end portion. Advantageously, the ribs provide for regions of controlled stress and strain when subjected to bending moments, which may be measured by the fiber optic strain gauges 904 embedded in the grooves 917 along the outer surface of the ribs and sensor body parallel to the lengthwise z-axis of tube 906.

In one example, tube 906 and the ribs may be comprised of material with a sufficiently low modulus of elasticity to give a sufficient strain signal under an applied load, a sufficiently high strain at yield to give adequate safety margin above the maximum design load, and a sufficiently high thermal diffusivity to promote rapid thermal equilibrium (therefore reducing thermal disturbances to sensor output signals) when subject to localized or asymmetric thermal disturbances from tissue contact or endoscope illumination. In particular, the plurality of radial ribs may be comprised of a high thermal diffusivity material, such as an aluminum alloy (e.g., 6061-T6 aluminum) or a copper alloy (e.g., GlidCop® AL-60) or a silver alloy to reduce the temperature difference between opposing gauges under transient thermal disturbances by providing a direct thermal pathway between opposing gauges. In yet another example, the plurality of fiber optic gauges 904 may be comprised of a negative thermo-optic coefficient optical fiber material, such as binary or ternary phosphate glass fiber, fluoride glass fiber, oxy-fluoride glass fiber, tellurite glass fiber, or a polymer fiber. The negative thermo-optic coefficient fiber advantageously reduces or eliminates the combined effect of a positive thermo-optic coefficient fiber, such as SMF-28 or other doped fiber, and the positive thermal expansion coefficient of the sensor body material.

In one example, tube 906 may be comprised of metal alloys, treated metals, or plated metals, such as of aluminum, copper, or silver, which allow for adequate strain, mechanical failure safety margin, and high thermal diffusivity. In a further example, 6061-T6 aluminum, which is an aluminum alloy that is heat treated and aged, GlidCop® AL-60, which is copper that is dispersion strengthened with ultrafine particles of aluminum oxide, or a dispersion strengthened silver, may be used to form both tube 906 and the plurality of ribs. Accordingly, both the plurality of ribs and the tube 906 may be comprised of a high thermal diffusivity material, such as an aluminum alloy (e.g., 6061-T6 aluminum) or a copper alloy (e.g., GlidCop® AL-60) or a silver alloy, to reduce transient and/or steady-state temperature differences between groups of strain gauges separated along the z-axis.

Similar to the embodiment described above with respect to FIGS. 6A-6C1, a thermal shielding may be provided over the strain gauges 904 in accordance with another embodiment of the present invention. In one example, a thermal shunt shell 952 is provided over tube 906 with an insulating fluid (gas or liquid) filled or evacuated gap 950 being provided between the outer surface of tube 906 and the inner surface of thermal shunt shell 952. Thermal shunt shell 952 may be mechanically and thermally isolated from the strain gauges by providing compliant elastomer rings 930 between the shunt shell 952 and the tube 906 to prevent interference with the applied surgical forces and to insulate the sensor.

In this embodiment, thermal shunt shell 952 includes an annular heat conducting rib 954 midway between strain gauges 904 in the axial direction (i.e., the z-axis direction). Heat conducting rib 954 contacts an outer surface of tube 906 and conducts heat from the outer shunt shell to the tube 906 such that external thermal disturbances will be more uniformly diffused among the sensors. In one example, heat conducting rib 954 may be comprised of the same material as thermal shunt shell 952, which may be comprised of a high diffusivity material, such as an aluminum alloy (e.g., 6061-T6 aluminum) or a copper alloy (e.g., GlidCop® AL-60) or a silver alloy. Heat conducting rib 954 may be comprised of a different material than thermal shunt shell 952 in other embodiments but will be comprised of a high thermal diffusivity material. Advantageously, the thermal shielding with heat conducting rib midway between the groups of strain gauges as described above allows for more uniform heat/thermal diffusion among the sensors, being particularly advantageous for mitigating asymmetric or transient thermal loads upon the instrument. The thermal shielding described above is applicable for various embodiments of the present invention.

Optionally, a light reflective surface or coating may be provided over thermal shunt shell 952, which may deflect light and reduce localized heating of the force sensor apparatus, for example from endoscope illumination. An insulating coating may also be provided over thermal shunt shell 952, the insulating coating being comprised of a substantially transparent plastic shrink polymer in one example.

Embodiments described above illustrate but do not limit the invention. It should also be understood that numerous modifications and variations are possible in accordance with the principles of the present invention. For example, the number of strain gauges and their configuration may vary but must allow for applicable force and torque determinations and noise rejection. Similarly, the number of ribs and angle between ribs may vary from those described above. Furthermore, the embodiments of force sensor apparatus described above may be integrated with a surgical instrument upon manufacture as a non-separable part of the shaft. Accordingly, the scope of the invention is defined only by the following claims.

I claim:

1. A force sensor apparatus, comprising: a tube portion including an outer surface, a plurality of radial ribs, and at least one fiber optic strain gauge positioned on the outer surface over each rib of the plurality of radial ribs, wherein the strain gauges are comprised of a negative thermo-optic coefficient optical fiber material; a proximal end of the tube portion being configured to operably couple to a shaft of a surgical instrument, the shaft being configured to operably couple to a manipulator arm of a robotic surgical system; and a distal end of the tube portion being configured to operably couple to a proximal end of a wrist joint so that the force sensor apparatus is positioned between the shaft and the wrist joint, and the wrist being configured to operably couple to an end effector.

2. The apparatus of claim 1, wherein the negative thermo-optic coefficient optical fiber material is selected from the group consisting of a binary or ternary phosphate glass, a fluoride glass, an oxy-fluoride glass, a tellurite glass, and a polymer.

3. The apparatus of claim 1, wherein the plurality of radial ribs includes one selected from the group consisting of four ribs spaced apart by pairs of supplementary angles about a lengthwise axis of the shaft and three ribs spaced apart by about 120 degrees about a lengthwise axis of the shaft.

4. The apparatus of claim 1, wherein the plurality of radial ribs includes eight ribs in two groups of four exposed ribs, with each of the ribs in a group being spaced apart by pairs of supplementary angles about a lengthwise axis of the tube portion.

5. The apparatus of claim 1, wherein the plurality of radial ribs includes six ribs in two groups of three exposed ribs, with each of the ribs in a group being spaced apart by about 120 degrees about a lengthwise axis of the tube portion.

6. The apparatus of claim 1, further comprising at least one aperture on the tube portion that exposes at least one of the plurality of radial ribs.

7. A force sensor apparatus, comprising: a tube portion including an outer surface, a plurality of radial ribs, and at least one pair of adjacent fiber optic strain gauges, each fiber optic strain gauge in the at least one pair being positioned on the outer surface over a rib of the plurality of radial ribs; a proximal end of the tube portion being configured to operably couple to a shaft of a surgical instrument, the shaft being configured to operably couple to a manipulator arm of a robotic surgical system; and a distal end of the tube portion being configured to operably couple to a proximal end of a wrist joint so that the force sensor apparatus is positioned between the shaft and the wrist joint, and the wrist being configured to operably couple to an end effector.

8. The apparatus of claim 7, wherein a first strain gauge of the at least one pair being configured to be unstrained, and the first strain gauge the at least one pair being configured as a local thermal correction reference for a second strain sensing gauge of the at least one pair.

9. The apparatus in claim 7, the at least one pair being in two separate adjacent fibers having different thermo-optic coefficients.

10. The apparatus of claim 7, the at least one pair being in two separate adjacent fibers with different core doping.

11. The apparatus of claim 7, the at least one pair being in butt fusion spliced fibers having different thermo-optic coefficients.

12. The apparatus of claim 7, the at least one pair being in adjacent cores of the same fiber, each core having a different thermo-optic coefficient.

13. The apparatus of claim 7, the at least one pair being coincident in orthogonal polarization directions of the same region of a sufficiently bi-refringent stress rod optical fiber.

14. The apparatus of claim 7, the at least one pair being coincident in orthogonal polarization directions of the same region of a sufficiently bi-refringent photonic crystal optical fiber.

15. The apparatus of claim 7, the at least one pair being coincident in the same fiber core region, and each strain gauge in the at least one pair having a different thermo-optic coefficient.

* * * * *